US012616474B2

(12) United States Patent
Fowler et al.

(10) Patent No.: US 12,616,474 B2
(45) Date of Patent: May 5, 2026

(54) ROBOTIC OR POWERED SURGICAL STAPLER WITH PREDICTIVE STAPLING END STOP

(71) Applicant: Covidien LP, Mansfield, MA (US)

(72) Inventors: David N. Fowler, Cheshire, CT (US); Matthew S. Eschbach, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/912,805

(22) Filed: Oct. 11, 2024

(65) Prior Publication Data

US 2025/0120717 A1 Apr. 17, 2025

Related U.S. Application Data

(60) Provisional application No. 63/590,814, filed on Oct. 17, 2023.

(51) Int. Cl.
*A61B 17/072* (2006.01)
*A61B 34/30* (2016.01)
(Continued)

(52) U.S. Cl.
CPC ........ *A61B 17/07207* (2013.01); *A61B 34/30* (2016.02); *G05D 3/12* (2013.01);
(Continued)

(58) Field of Classification Search
CPC .............. A61B 17/07207; A61B 34/30; A61B 2090/0811; A61B 2017/07257; A61B 2017/07271; G05D 3/12
See application file for complete search history.

(56) References Cited

U.S. PATENT DOCUMENTS

| | | |
|---|---|---|
| 37,165 A | 12/1862 | Gary |
| 3,209,754 A | 10/1965 | Brown |
| (Continued) | | |

FOREIGN PATENT DOCUMENTS

| | | |
|---|---|---|
| AU | 2018202813 A1 | 11/2018 |
| CN | 101683284 A | 3/2010 |
| (Continued) | | |

OTHER PUBLICATIONS

International Search Report and Written Opinion of the International Searching Authority issued in corresponding application PCT/IB2024/060097 mailed Feb. 6, 2025 (12 pages).
(Continued)

*Primary Examiner* — Michelle Lopez
(74) *Attorney, Agent, or Firm* — Carter, DeLuca & Farrell LLP

(57) ABSTRACT

A powered or robotic surgical stapler includes a loading unit having an end effector with an anvil and staple cartridge. A drive shaft disposed in the loading unit is actuated by one or more motors. The drive shaft approximates the anvil and advances a knife and a sled to eject a plurality of staples from the cartridge. A position sensor and a torque or current draw sensor measure operation of the motor and a processor determines an initial peak in the torque or current. The processor then calculates a stop position from the drive shaft based on a motor position corresponding to the initial peak and actuates the drive shaft until it reaches the stop position, which occurs prior to the drive shaft reaching a mechanical limit of the drive shaft.

17 Claims, 12 Drawing Sheets

(51) Int. Cl.
    *G05D 3/12*         (2006.01)
    *A61B 90/00*      (2016.01)
(52) U.S. Cl.
    CPC .............. *A61B 2017/07257* (2013.01); *A61B 2017/07271* (2013.01); *A61B 2090/0811* (2016.02)

(56) References Cited

U.S. PATENT DOCUMENTS

| | | | |
|---|---|---|---|
| 3,273,562 A | 9/1966 | Brown |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,731,058 A | 3/1988 | Doan |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,391,166 A | 2/1995 | Eggers |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,675 A | 11/1997 | Sawyer et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |

(56)                    References Cited

U.S. PATENT DOCUMENTS

| | | | |
|---|---|---|---|
| 5,704,534 | A | 1/1998 | Huitema et al. |
| 5,713,505 | A | 2/1998 | Huitema |
| 5,713,896 | A | 2/1998 | Nardella |
| 5,715,987 | A | 2/1998 | Kelley et al. |
| 5,716,366 | A | 2/1998 | Yates |
| 5,720,753 | A | 2/1998 | Sander et al. |
| 5,725,529 | A | 3/1998 | Nicholson et al. |
| 5,728,110 | A | 3/1998 | Vidal et al. |
| 5,728,116 | A | 3/1998 | Rosenman |
| 5,730,757 | A | 3/1998 | Benetti et al. |
| 5,735,848 | A | 4/1998 | Yates et al. |
| 5,738,474 | A | 4/1998 | Blewett |
| 5,755,726 | A | 5/1998 | Pratt et al. |
| 5,759,171 | A | 6/1998 | Coelho et al. |
| 5,779,130 | A | 7/1998 | Alesi et al. |
| 5,782,397 | A | 7/1998 | Koukline |
| 5,785,713 | A | 7/1998 | Jobe |
| 5,788,698 | A | 8/1998 | Savornin |
| 5,810,811 | A | 9/1998 | Yates et al. |
| 5,823,066 | A | 10/1998 | Huitema et al. |
| 5,829,662 | A | 11/1998 | Allen et al. |
| 5,830,121 | A | 11/1998 | Enomoto et al. |
| 5,849,023 | A | 12/1998 | Mericle |
| 5,849,028 | A | 12/1998 | Chen |
| 5,855,311 | A | 1/1999 | Hamblin et al. |
| 5,861,005 | A | 1/1999 | Kontos |
| 5,865,361 | A | 2/1999 | Milliman et al. |
| 5,876,401 | A | 3/1999 | Schulze et al. |
| 5,891,156 | A | 4/1999 | Gessner et al. |
| 5,893,813 | A | 4/1999 | Yamamoto |
| 5,895,396 | A | 4/1999 | Day et al. |
| 5,906,607 | A | 5/1999 | Taylor et al. |
| 5,911,721 | A | 6/1999 | Nicholson et al. |
| 5,918,791 | A | 7/1999 | Sorrentino et al. |
| 5,928,222 | A | 7/1999 | Kleinerman |
| 5,944,717 | A | 8/1999 | Lee et al. |
| 5,944,736 | A | 8/1999 | Taylor et al. |
| 5,954,259 | A | 9/1999 | Viola et al. |
| 5,961,521 | A | 10/1999 | Roger |
| 5,964,394 | A | 10/1999 | Robertson |
| 5,968,044 | A | 10/1999 | Nicholson et al. |
| 5,976,171 | A | 11/1999 | Taylor |
| 5,980,518 | A | 11/1999 | Carr et al. |
| 5,980,548 | A | 11/1999 | Evans et al. |
| 5,991,355 | A | 11/1999 | Dahlke |
| 5,991,650 | A | 11/1999 | Swanson et al. |
| 5,992,724 | A | 11/1999 | Snyder |
| 5,997,552 | A | 12/1999 | Person et al. |
| 6,004,335 | A | 12/1999 | Vaitekunas et al. |
| 6,007,550 | A | 12/1999 | Wang et al. |
| 6,010,054 | A | 1/2000 | Johnson et al. |
| 6,013,077 | A | 1/2000 | Harwin |
| 6,015,417 | A | 1/2000 | Reynolds, Jr. |
| 6,017,354 | A | 1/2000 | Culp et al. |
| 6,030,410 | A | 2/2000 | Zurbrugg |
| 6,032,849 | A | 3/2000 | Mastri et al. |
| 6,039,731 | A | 3/2000 | Taylor et al. |
| 6,051,007 | A | 4/2000 | Hogendijk et al. |
| 6,063,078 | A | 5/2000 | Wittkampf |
| 6,063,095 | A | 5/2000 | Wang et al. |
| 6,077,246 | A | 6/2000 | Kullas et al. |
| 6,079,606 | A | 6/2000 | Milliman et al. |
| 6,080,150 | A | 6/2000 | Gough |
| 6,083,242 | A | 7/2000 | Cook |
| 6,090,123 | A | 7/2000 | Culp et al. |
| 6,092,422 | A | 7/2000 | Binnig et al. |
| 6,109,500 | A | 8/2000 | Alli et al. |
| 6,113,592 | A | 9/2000 | Taylor |
| 6,123,702 | A | 9/2000 | Swanson et al. |
| H1904 | H | 10/2000 | Yates et al. |
| 6,126,058 | A | 10/2000 | Adams et al. |
| 6,126,651 | A | 10/2000 | Mayer |
| 6,127,811 | A | 10/2000 | Shenoy et al. |
| 6,132,368 | A | 10/2000 | Cooper |
| 6,132,425 | A | 10/2000 | Gough |
| 6,165,169 | A | 12/2000 | Panescu et al. |
| 6,166,538 | A | 12/2000 | D'Alfonso |
| 6,179,840 | B1 | 1/2001 | Bowman |
| 6,187,009 | B1 | 2/2001 | Herzog et al. |
| 6,187,019 | B1 | 2/2001 | Stefanchik et al. |
| 6,190,401 | B1 | 2/2001 | Green et al. |
| 6,193,501 | B1 | 2/2001 | Masel et al. |
| 6,202,914 | B1 | 3/2001 | Geiste et al. |
| 6,206,903 | B1 | 3/2001 | Ramans |
| 6,217,573 | B1 | 4/2001 | Webster |
| 6,228,534 | B1 | 5/2001 | Takeuchi et al. |
| 6,231,565 | B1 | 5/2001 | Tovey et al. |
| 6,236,874 | B1 | 5/2001 | Devlin et al. |
| 6,237,604 | B1 | 5/2001 | Burnside et al. |
| 6,241,139 | B1 | 6/2001 | Milliman et al. |
| 6,245,065 | B1 | 6/2001 | Panescu et al. |
| 6,246,200 | B1 | 6/2001 | Blumenkranz et al. |
| 6,248,117 | B1 | 6/2001 | Blatter |
| 6,250,532 | B1 | 6/2001 | Green et al. |
| 6,258,111 | B1 | 7/2001 | Ross et al. |
| 6,264,086 | B1 | 7/2001 | McGuckin, Jr. |
| 6,264,087 | B1 | 7/2001 | Whitman |
| 6,264,653 | B1 | 7/2001 | Falwell |
| 6,281,471 | B1 | 8/2001 | Smart |
| 6,288,534 | B1 | 9/2001 | Starkweather et al. |
| 6,290,701 | B1 | 9/2001 | Enayati |
| 6,293,943 | B1 | 9/2001 | Panescu et al. |
| 6,295,330 | B1 | 9/2001 | Skog et al. |
| 6,312,435 | B1 | 11/2001 | Wallace et al. |
| 6,315,184 | B1 | 11/2001 | Whitman |
| 6,329,778 | B1 | 12/2001 | Culp et al. |
| 6,330,965 | B1 | 12/2001 | Milliman et al. |
| 6,331,181 | B1 | 12/2001 | Tierney et al. |
| 6,346,104 | B2 | 2/2002 | Daly et al. |
| 6,355,066 | B1 | 3/2002 | Kim |
| 6,364,884 | B1 | 4/2002 | Bowman et al. |
| 6,387,092 | B1 | 5/2002 | Burnside et al. |
| 6,388,240 | B2 | 5/2002 | Schulz et al. |
| 6,394,998 | B1 | 5/2002 | Wallace et al. |
| 6,402,766 | B2 | 6/2002 | Bowman et al. |
| H2037 | H | 7/2002 | Yates et al. |
| 6,412,279 | B1 | 7/2002 | Coleman et al. |
| 6,424,885 | B1 | 7/2002 | Niemeyer et al. |
| 6,425,903 | B1 | 7/2002 | Voegele |
| 6,436,097 | B1 | 8/2002 | Nardella |
| 6,436,107 | B1 | 8/2002 | Wang et al. |
| 6,436,110 | B2 | 8/2002 | Bowman et al. |
| 6,441,577 | B2 | 8/2002 | Blumenkranz et al. |
| 6,443,973 | B1 | 9/2002 | Whitman |
| 6,447,517 | B1 | 9/2002 | Bowman |
| 6,459,926 | B1 | 10/2002 | Nowlin et al. |
| 6,461,372 | B1 | 10/2002 | Jensen et al. |
| 6,478,210 | B2 | 11/2002 | Adams et al. |
| 6,491,691 | B1 | 12/2002 | Morley et al. |
| 6,491,701 | B2 | 12/2002 | Tierney et al. |
| 6,493,608 | B1 | 12/2002 | Niemeyer |
| 6,497,707 | B1 | 12/2002 | Bowman et al. |
| 6,505,768 | B2 | 1/2003 | Whitman |
| 6,515,273 | B2 | 2/2003 | Al-Ali |
| 6,524,316 | B1 | 2/2003 | Nicholson et al. |
| 6,533,157 | B1 | 3/2003 | Whitman |
| 6,540,751 | B2 | 4/2003 | Enayati |
| 6,544,273 | B1 | 4/2003 | Harari et al. |
| 6,554,852 | B1 | 4/2003 | Oberlander |
| 6,562,071 | B2 | 5/2003 | Jarvinen |
| 6,565,554 | B1 | 5/2003 | Niemeyer |
| 6,578,579 | B2 | 6/2003 | Burnside et al. |
| 6,601,748 | B1 | 8/2003 | Fung et al. |
| 6,601,749 | B2 | 8/2003 | Sullivan et al. |
| 6,602,252 | B2 | 8/2003 | Mollenauer |
| 6,611,793 | B1 | 8/2003 | Burnside et al. |
| 6,616,821 | B2 | 9/2003 | Broadley et al. |
| 6,629,986 | B1 | 10/2003 | Ross et al. |
| 6,645,196 | B1 | 11/2003 | Nixon et al. |
| 6,651,669 | B1 | 11/2003 | Burnside |
| 6,656,177 | B2 | 12/2003 | Truckai et al. |
| 6,659,939 | B2 | 12/2003 | Moll |
| 6,669,073 | B2 | 12/2003 | Milliman et al. |
| 6,669,705 | B2 | 12/2003 | Westhaver et al. |

(56)                    References Cited

U.S. PATENT DOCUMENTS

| | | | |
|---|---|---|---|
| 6,671,581 B2 | 12/2003 | Niemeyer et al. |
| 6,676,684 B1 | 1/2004 | Morley et al. |
| 6,685,698 B2 | 2/2004 | Morley et al. |
| 6,696,008 B2 | 2/2004 | Brandinger |
| 6,698,643 B2 | 3/2004 | Whitman |
| 6,699,177 B1 | 3/2004 | Wang et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,736,085 B1 | 5/2004 | Esnouf |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,792,390 B1 | 9/2004 | Burnside et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,817,508 B1 | 11/2004 | Racenet et al. |
| 6,830,174 B2 | 12/2004 | Hillstead et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |
| 6,866,671 B2 | 3/2005 | Tierney et al. |
| 6,871,117 B2 | 3/2005 | Wang et al. |
| 6,872,214 B2 | 3/2005 | Sonnenschein et al. |
| 6,879,880 B2 | 4/2005 | Nowlin et al. |
| 6,899,538 B2 | 5/2005 | Matoba |
| 6,899,705 B2 | 5/2005 | Niemeyer |
| 6,900,004 B2 | 5/2005 | Satake |
| 6,902,560 B1 | 6/2005 | Morley et al. |
| 6,905,057 B2 | 6/2005 | Swayze et al. |
| 6,926,636 B2 | 8/2005 | Luper |
| 6,936,042 B2 | 8/2005 | Wallace et al. |
| 6,951,535 B2 | 10/2005 | Ghodoussi et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,974,449 B2 | 12/2005 | Niemeyer |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 6,991,627 B2 | 1/2006 | Madhani et al. |
| 6,994,708 B2 | 2/2006 | Manzo |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,048,745 B2 | 5/2006 | Tierney et al. |
| 7,055,731 B2 | 6/2006 | Shelton, IV et al. |
| 7,059,508 B2 | 6/2006 | Shelton, IV et al. |
| 7,066,926 B2 | 6/2006 | Wallace et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,118,582 B1 | 10/2006 | Wang et al. |
| 7,122,029 B2 | 10/2006 | Koop et al. |
| 7,125,403 B2 | 10/2006 | Julian et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,155,315 B2 | 12/2006 | Niemeyer et al. |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,239,940 B2 | 7/2007 | Wang et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,306,597 B2 | 12/2007 | Manzo |
| 7,328,828 B2 | 2/2008 | Ortiz et al. |
| 7,335,169 B2 | 2/2008 | Thompson et al. |
| 7,357,774 B2 | 4/2008 | Cooper |
| 7,364,061 B2 | 4/2008 | Swayze et al. |
| 7,373,219 B2 | 5/2008 | Nowlin et al. |
| 7,379,790 B2 | 5/2008 | Toth et al. |
| 7,380,695 B2 | 6/2008 | Doll et al. |
| 7,380,696 B2 | 6/2008 | Shelton, IV et al. |
| 7,386,365 B2 | 6/2008 | Nixon |
| 7,391,173 B2 | 6/2008 | Schena |
| 7,398,707 B2 | 7/2008 | Morley et al. |
| 7,404,508 B2 | 7/2008 | Smith et al. |
| 7,413,565 B2 | 8/2008 | Wang et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,453,227 B2 | 11/2008 | Prisco et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,524,320 B2 | 4/2009 | Tierney et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,666,191 B2 | 2/2010 | Orban, III et al. |
| 7,670,334 B2 | 3/2010 | Hueil et al. |
| 7,682,357 B2 | 3/2010 | Ghodoussi et al. |
| 7,689,320 B2 | 3/2010 | Prisco et al. |
| 7,694,809 B2 | 4/2010 | Garbini et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,721,931 B2 | 5/2010 | Shelton, IV et al. |
| 7,725,214 B2 | 5/2010 | Diolaiti |
| 7,727,244 B2 | 6/2010 | Orban et al. |
| 7,740,159 B2 | 6/2010 | Shelton, IV et al. |
| 7,741,802 B2 | 6/2010 | Prisco |
| 7,753,248 B2 | 7/2010 | Viola |
| 7,756,036 B2 | 7/2010 | Druke et al. |
| 7,757,028 B2 | 7/2010 | Druke et al. |
| 7,757,925 B2 | 7/2010 | Viola et al. |
| 7,762,825 B2 | 7/2010 | Burbank et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,778,733 B2 | 8/2010 | Nowlin et al. |
| 7,784,663 B2 | 8/2010 | Shelton, IV |
| 7,803,151 B2 | 9/2010 | Whitman |
| 7,806,891 B2 | 10/2010 | Nowlin et al. |

(56)                    References Cited

U.S. PATENT DOCUMENTS

| | | | |
|---|---|---|---|
| 7,815,090 B2 | 10/2010 | Marczyk |
| 7,819,859 B2 | 10/2010 | Prisco et al. |
| 7,819,885 B2 | 10/2010 | Cooper |
| 7,823,760 B2 | 11/2010 | Zemlok et al. |
| 7,824,401 B2 | 11/2010 | Manzo et al. |
| 7,835,823 B2 | 11/2010 | Sillman et al. |
| 7,843,158 B2 | 11/2010 | Prisco |
| 7,845,534 B2 | 12/2010 | Viola et al. |
| 7,865,266 B2 | 1/2011 | Moll et al. |
| 7,865,269 B2 | 1/2011 | Prisco et al. |
| 7,870,989 B2 | 1/2011 | Viola et al. |
| 7,886,743 B2 | 2/2011 | Cooper et al. |
| 7,886,953 B2 | 2/2011 | Schwemberger et al. |
| 7,887,530 B2 | 2/2011 | Zemlok et al. |
| 7,899,578 B2 | 3/2011 | Prisco et al. |
| 7,905,897 B2 | 3/2011 | Whitman et al. |
| 7,907,166 B2 | 3/2011 | Lamprecht et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,935,130 B2 | 5/2011 | Williams |
| 7,950,560 B2 | 5/2011 | Zemlok et al. |
| 7,955,352 B2 | 6/2011 | McEwen et al. |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,006,885 B2 | 8/2011 | Marczyk |
| 8,006,887 B2 | 8/2011 | Marczyk |
| 8,011,551 B2 | 9/2011 | Marczyk et al. |
| 8,012,170 B2 | 9/2011 | Whitman et al. |
| 8,020,742 B2 | 9/2011 | Marczyk |
| 8,025,199 B2 | 9/2011 | Whitman et al. |
| 8,038,044 B2 | 10/2011 | Viola |
| 8,052,024 B2 | 11/2011 | Viola et al. |
| 8,054,752 B2 | 11/2011 | Druke et al. |
| 8,062,288 B2 | 11/2011 | Cooper et al. |
| 8,066,721 B2 | 11/2011 | Kortenbach et al. |
| 8,074,858 B2 | 12/2011 | Marczyk |
| 8,079,950 B2 | 12/2011 | Stern et al. |
| 8,092,493 B2 | 1/2012 | Marczyk |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,128,645 B2 | 3/2012 | Sonnenschein et al. |
| 8,132,705 B2 | 3/2012 | Viola et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,157,150 B2 | 4/2012 | Viola et al. |
| 8,182,469 B2 | 5/2012 | Anderson et al. |
| 8,186,555 B2 | 5/2012 | Shelton, IV et al. |
| 8,201,721 B2 | 6/2012 | Zemlok et al. |
| 8,202,278 B2 | 6/2012 | Orban, III et al. |
| 8,206,406 B2 | 6/2012 | Orban, III |
| 8,210,412 B2 | 7/2012 | Marczyk |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,240,536 B2 | 8/2012 | Marczyk |
| 8,240,537 B2 | 8/2012 | Marczyk |
| 8,256,319 B2 | 9/2012 | Cooper et al. |
| 8,267,924 B2 | 9/2012 | Zemlok et al. |
| 8,285,517 B2 | 10/2012 | Sillman et al. |
| 8,315,720 B2 | 11/2012 | Mohr et al. |
| 8,328,823 B2 | 12/2012 | Aranyi et al. |
| 8,335,590 B2 | 12/2012 | Costa et al. |
| 8,347,757 B2 | 1/2013 | Duval |
| 8,348,125 B2 | 1/2013 | Viola et al. |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,685,004 B2 | 4/2014 | Zemlock et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,192,381 B2 | 11/2015 | Marczyk |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |

(56) References Cited

U.S. PATENT DOCUMENTS

| | | | |
|---|---|---|---|
| 9,265,584 | B2 | 2/2016 | Itkowitz et al. |
| 9,283,049 | B2 | 3/2016 | Diolaiti et al. |
| 9,301,811 | B2 | 4/2016 | Goldberg et al. |
| 9,314,307 | B2 | 4/2016 | Richmond et al. |
| 9,317,651 | B2 | 4/2016 | Nixon |
| 9,345,546 | B2 | 5/2016 | Toth et al. |
| 9,364,222 | B2 | 6/2016 | Zemlok et al. |
| 9,370,360 | B2 | 6/2016 | Marczyk |
| 9,370,361 | B2 | 6/2016 | Viola et al. |
| 9,393,017 | B2 | 7/2016 | Flanagan et al. |
| 9,402,689 | B2 | 8/2016 | Prisco et al. |
| 9,417,621 | B2 | 8/2016 | Diolaiti |
| 9,424,303 | B2 | 8/2016 | Hoffman et al. |
| 9,433,415 | B2 | 9/2016 | Marczyk et al. |
| 9,433,418 | B2 | 9/2016 | Whitman et al. |
| 9,446,517 | B2 | 9/2016 | Burns et al. |
| 9,452,020 | B2 | 9/2016 | Griffiths et al. |
| 9,474,569 | B2 | 10/2016 | Manzo et al. |
| 9,480,492 | B2 | 11/2016 | Aranyi et al. |
| 9,480,533 | B2 | 11/2016 | Devengenzo et al. |
| 9,503,713 | B2 | 11/2016 | Zhao et al. |
| 9,550,300 | B2 | 1/2017 | Danitz et al. |
| 9,554,859 | B2 | 1/2017 | Nowlin et al. |
| 9,566,124 | B2 | 2/2017 | Prisco et al. |
| 9,579,164 | B2 | 2/2017 | Itkowitz et al. |
| 9,585,641 | B2 | 3/2017 | Cooper et al. |
| 9,585,659 | B2 | 3/2017 | Viola et al. |
| 9,615,883 | B2 | 4/2017 | Schena et al. |
| 9,623,563 | B2 | 4/2017 | Nixon |
| 9,623,902 | B2 | 4/2017 | Griffiths et al. |
| 9,629,520 | B2 | 4/2017 | Diolaiti |
| 9,662,177 | B2 | 5/2017 | Weir et al. |
| 9,664,262 | B2 | 5/2017 | Donlon et al. |
| 9,675,354 | B2 | 6/2017 | Weir et al. |
| 9,687,312 | B2 | 6/2017 | Dachs, II et al. |
| 9,700,334 | B2 | 7/2017 | Hinman et al. |
| 9,718,190 | B2 | 8/2017 | Larkin et al. |
| 9,730,719 | B2 | 8/2017 | Brisson et al. |
| 9,737,199 | B2 | 8/2017 | Pistor et al. |
| 9,795,446 | B2 | 10/2017 | DiMaio et al. |
| 9,797,484 | B2 | 10/2017 | Solomon et al. |
| 9,801,690 | B2 | 10/2017 | Larkin et al. |
| 9,814,530 | B2 | 11/2017 | Weir et al. |
| 9,814,536 | B2 | 11/2017 | Goldberg et al. |
| 9,814,537 | B2 | 11/2017 | Itkowitz et al. |
| 9,820,823 | B2 | 11/2017 | Richmond et al. |
| 9,827,059 | B2 | 11/2017 | Robinson et al. |
| 9,830,371 | B2 | 11/2017 | Hoffman et al. |
| 9,839,481 | B2 | 12/2017 | Blumenkranz et al. |
| 9,839,487 | B2 | 12/2017 | Dachs, II |
| 9,850,994 | B2 | 12/2017 | Schena |
| 9,855,102 | B2 | 1/2018 | Blumenkranz |
| 9,855,107 | B2 | 1/2018 | Labonville et al. |
| 9,872,737 | B2 | 1/2018 | Nixon |
| 9,877,718 | B2 | 1/2018 | Weir et al. |
| 9,883,920 | B2 | 2/2018 | Blumenkranz |
| 9,888,974 | B2 | 2/2018 | Niemeyer |
| 9,895,813 | B2 | 2/2018 | Blumenkranz et al. |
| 9,901,408 | B2 | 2/2018 | Larkin |
| 9,918,800 | B2 | 3/2018 | Itkowitz et al. |
| 9,943,375 | B2 | 4/2018 | Blumenkranz et al. |
| 9,948,852 | B2 | 4/2018 | Lilagan et al. |
| 9,949,798 | B2 | 4/2018 | Weir |
| 9,949,802 | B2 | 4/2018 | Cooper |
| 9,952,107 | B2 | 4/2018 | Blumenkranz et al. |
| 9,956,044 | B2 | 5/2018 | Gomez et al. |
| 9,962,157 | B2 | 5/2018 | Sapre |
| 9,980,778 | B2 | 5/2018 | Ohline et al. |
| 10,008,017 | B2 | 6/2018 | Itkowitz et al. |
| 10,028,793 | B2 | 7/2018 | Griffiths et al. |
| 10,033,308 | B2 | 7/2018 | Chaghajerdi et al. |
| 10,034,719 | B2 | 7/2018 | Richmond et al. |
| 10,052,167 | B2 | 8/2018 | Au et al. |
| 10,085,811 | B2 | 10/2018 | Weir et al. |
| 10,092,165 | B2 | 10/2018 | Power |
| 10,092,344 | B2 | 10/2018 | Mohr et al. |
| 10,123,844 | B2 | 11/2018 | Nowlin |
| 10,188,471 | B2 | 1/2019 | Brisson |
| 10,201,390 | B2 | 2/2019 | Swarup et al. |
| 10,213,202 | B2 | 2/2019 | Flanagan et al. |
| 10,238,386 | B2 | 3/2019 | Overmyer et al. |
| 10,258,416 | B2 | 4/2019 | Mintz et al. |
| 10,278,782 | B2 | 5/2019 | Jarc et al. |
| 10,278,783 | B2 | 5/2019 | Itkowitz et al. |
| 10,282,881 | B2 | 5/2019 | Itkowitz et al. |
| 10,335,242 | B2 | 7/2019 | Devengenzo et al. |
| 10,390,858 | B2 | 8/2019 | Evans et al. |
| 10,405,934 | B2 | 9/2019 | Prisco et al. |
| 10,433,922 | B2 | 10/2019 | Itkowitz et al. |
| 10,464,219 | B2 | 11/2019 | Robinson et al. |
| 10,485,621 | B2 | 11/2019 | Morrissette et al. |
| 10,492,814 | B2 | 12/2019 | Snow et al. |
| 10,500,004 | B2 | 12/2019 | Hanuschik et al. |
| 10,500,005 | B2 | 12/2019 | Weir et al. |
| 10,500,007 | B2 | 12/2019 | Richmond et al. |
| 10,507,066 | B2 | 12/2019 | DiMaio et al. |
| 10,510,267 | B2 | 12/2019 | Jarc et al. |
| 10,524,871 | B2 | 1/2020 | Liao |
| 10,548,459 | B2 | 2/2020 | Itkowitz et al. |
| 10,575,909 | B2 | 3/2020 | Robinson et al. |
| 10,592,529 | B2 | 3/2020 | Hoffman et al. |
| 10,595,946 | B2 | 3/2020 | Nixon |
| 10,722,222 | B2 | 7/2020 | Aranyi |
| 10,881,469 | B2 | 1/2021 | Robinson |
| 10,881,473 | B2 | 1/2021 | Itkowitz et al. |
| 10,898,188 | B2 | 1/2021 | Burbank |
| 10,898,189 | B2 | 1/2021 | McDonald, II |
| 10,905,506 | B2 | 2/2021 | Itkowitz et al. |
| 10,912,544 | B2 | 2/2021 | Brisson et al. |
| 10,912,619 | B2 | 2/2021 | Jarc et al. |
| 10,918,387 | B2 | 2/2021 | Duque et al. |
| 10,918,449 | B2 | 2/2021 | Solomon et al. |
| 10,932,873 | B2 | 3/2021 | Griffiths et al. |
| 10,932,877 | B2 | 3/2021 | Devengenzo et al. |
| 10,939,969 | B2 | 3/2021 | Swarup et al. |
| 10,939,973 | B2 | 3/2021 | DiMaio et al. |
| 10,952,801 | B2 | 3/2021 | Miller et al. |
| 10,965,933 | B2 | 3/2021 | Jarc |
| 10,966,742 | B2 | 4/2021 | Rosa et al. |
| 10,973,517 | B2 | 4/2021 | Wixey |
| 10,973,519 | B2 | 4/2021 | Weir et al. |
| 10,984,567 | B2 | 4/2021 | Itkowitz et al. |
| 10,993,773 | B2 | 5/2021 | Cooper et al. |
| 10,993,775 | B2 | 5/2021 | Cooper et al. |
| 11,000,331 | B2 | 5/2021 | Krom et al. |
| 11,013,567 | B2 | 5/2021 | Wu et al. |
| 11,020,138 | B2 | 6/2021 | Ragosta |
| 11,020,191 | B2 | 6/2021 | Diolaiti et al. |
| 11,020,193 | B2 | 6/2021 | Wixey et al. |
| 11,026,755 | B2 | 6/2021 | Weir et al. |
| 11,026,759 | B2 | 6/2021 | Donlon et al. |
| 11,040,189 | B2 | 6/2021 | Vaders et al. |
| 11,045,077 | B2 | 6/2021 | Stern et al. |
| 11,045,274 | B2 | 6/2021 | Dachs, II et al. |
| 11,058,501 | B2 | 7/2021 | Tokarchuk et al. |
| 11,076,925 | B2 | 8/2021 | DiMaio et al. |
| 11,090,119 | B2 | 8/2021 | Burbank |
| 11,096,687 | B2 | 8/2021 | Flanagan et al. |
| 11,098,803 | B2 | 8/2021 | Duque et al. |
| 11,109,925 | B2 | 9/2021 | Cooper et al. |
| 11,116,578 | B2 | 9/2021 | Hoffman et al. |
| 11,129,683 | B2 | 9/2021 | Steger et al. |
| 11,135,029 | B2 | 10/2021 | Suresh et al. |
| 11,147,552 | B2 | 10/2021 | Burbank et al. |
| 11,147,640 | B2 | 10/2021 | Jarc et al. |
| 11,154,373 | B2 | 10/2021 | Abbott et al. |
| 11,154,374 | B2 | 10/2021 | Hanuschik et al. |
| 11,160,622 | B2 | 11/2021 | Goldberg et al. |
| 11,160,625 | B2 | 11/2021 | Wixey et al. |
| 11,161,243 | B2 | 11/2021 | Rabindran et al. |
| 11,166,758 | B2 | 11/2021 | Mohr et al. |
| 11,166,770 | B2 | 11/2021 | DiMaio et al. |
| 11,166,773 | B2 | 11/2021 | Ragosta et al. |
| 11,173,597 | B2 | 11/2021 | Rabindran et al. |

(56) References Cited

U.S. PATENT DOCUMENTS

| | | | |
|---|---|---|---|
| 11,185,378 B2 | 11/2021 | Weir et al. | |
| 11,191,596 B2 | 12/2021 | Thompson et al. | |
| 11,197,729 B2 | 12/2021 | Thompson et al. | |
| 11,213,360 B2 | 1/2022 | Hourtash et al. | |
| 11,221,863 B2 | 1/2022 | Azizian et al. | |
| 11,234,700 B2 | 2/2022 | Ragosta et al. | |
| 11,241,274 B2 | 2/2022 | Vaders et al. | |
| 11,241,290 B2 | 2/2022 | Waterbury et al. | |
| 11,259,870 B2 | 3/2022 | DiMaio et al. | |
| 11,259,884 B2 | 3/2022 | Burbank | |
| 11,272,993 B2 | 3/2022 | Gomez et al. | |
| 11,272,994 B2 | 3/2022 | Saraliev et al. | |
| 11,291,442 B2 | 4/2022 | Wixey et al. | |
| 11,291,513 B2 | 4/2022 | Manzo et al. | |
| 11,376,002 B2 | 7/2022 | Shelton, IV et al. | |
| 11,376,098 B2 | 7/2022 | Shelton, IV et al. | |
| 11,381,759 B2 | 7/2022 | Zhao et al. | |
| 11,382,621 B2 | 7/2022 | Scheib et al. | |
| 11,382,624 B2 | 7/2022 | Harris et al. | |
| 11,382,625 B2 | 7/2022 | Huitema et al. | |
| 11,382,626 B2 | 7/2022 | Shelton, IV et al. | |
| 11,382,627 B2 | 7/2022 | Huitema et al. | |
| 11,382,638 B2 | 7/2022 | Harris et al. | |
| 11,382,644 B2 | 7/2022 | Schoettgen et al. | |
| 11,389,160 B2 | 7/2022 | Shelton, IV et al. | |
| 11,389,255 B2 | 7/2022 | DiMaio et al. | |
| 11,399,906 B2 | 8/2022 | Shelton, IV et al. | |
| 11,406,379 B2 | 8/2022 | Hess et al. | |
| 11,410,259 B2 | 8/2022 | Harris et al. | |
| 11,419,630 B2 | 8/2022 | Yates et al. | |
| 11,424,027 B2 | 8/2022 | Shelton, IV | |
| 11,432,888 B2 | 9/2022 | Diolaiti et al. | |
| 11,432,893 B2 | 9/2022 | Itkowitz et al. | |
| 11,432,895 B2 | 9/2022 | Loh et al. | |
| 11,439,390 B2 | 9/2022 | Patel et al. | |
| 11,439,391 B2 | 9/2022 | Bruns et al. | |
| 11,468,791 B2 | 10/2022 | Jarc et al. | |
| 11,471,155 B2 | 10/2022 | Shelton, IV et al. | |
| 11,471,221 B2 | 10/2022 | Zhao et al. | |
| 11,478,308 B2 | 10/2022 | Hoffman et al. | |
| 11,490,977 B2 | 11/2022 | Schena et al. | |
| 11,497,499 B2 | 11/2022 | Shelton, IV et al. | |
| 11,504,119 B2 | 11/2022 | Shelton, IV et al. | |
| 11,504,124 B2 | 11/2022 | Patel et al. | |
| 11,510,743 B2 | 11/2022 | Shelton, IV et al. | |
| 11,517,312 B2 | 12/2022 | Wixey | |
| 11,517,325 B2 | 12/2022 | Shelton, IV et al. | |
| 11,518,048 B2 | 12/2022 | Saraliev et al. | |
| 2002/0103489 A1 | 8/2002 | Ku | |
| 2002/0111641 A1 | 8/2002 | Peterson et al. | |
| 2002/0165541 A1 | 11/2002 | Whitman | |
| 2003/0090201 A1 | 5/2003 | Peng | |
| 2003/0114851 A1 | 6/2003 | Truckai et al. | |
| 2003/0120306 A1 | 6/2003 | Burbank et al. | |
| 2004/0232201 A1 | 11/2004 | Wenchell et al. | |
| 2005/0006429 A1 | 1/2005 | Wales et al. | |
| 2005/0010235 A1 | 1/2005 | VanDusseldorp | |
| 2005/0131390 A1 | 6/2005 | Heinrich et al. | |
| 2005/0139636 A1 | 6/2005 | Schwemberger et al. | |
| 2005/0177176 A1 | 8/2005 | Gerbi et al. | |
| 2005/0192609 A1 | 9/2005 | Whitman et al. | |
| 2005/0247753 A1 | 11/2005 | Kelly et al. | |
| 2006/0000867 A1 | 1/2006 | Shelton et al. | |
| 2007/0023477 A1 | 2/2007 | Whitman et al. | |
| 2007/0029363 A1 | 2/2007 | Popov | |
| 2007/0084897 A1 | 4/2007 | Shelton et al. | |
| 2007/0102472 A1 | 5/2007 | Shelton | |
| 2007/0175949 A1 | 8/2007 | Shelton et al. | |
| 2007/0175950 A1 | 8/2007 | Shelton et al. | |
| 2007/0175951 A1 | 8/2007 | Shelton et al. | |
| 2007/0175955 A1 | 8/2007 | Shelton et al. | |
| 2007/0219563 A1 | 9/2007 | Voegele | |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0135600 A1 | 6/2008 | Hiranuma et al. | |
| 2008/0169329 A1 | 7/2008 | Shelton et al. | |
| 2008/0185419 A1 | 8/2008 | Smith et al. | |
| 2008/0197167 A1 | 8/2008 | Viola et al. | |
| 2008/0255413 A1 | 10/2008 | Zemlok et al. | |
| 2008/0255607 A1 | 10/2008 | Zemlok | |
| 2009/0018624 A1 | 1/2009 | Levinson et al. | |
| 2009/0090201 A1 | 4/2009 | Viola | |
| 2009/0090763 A1 | 4/2009 | Zemlok et al. | |
| 2010/0200636 A1 | 8/2010 | Zemlok et al. | |
| 2010/0312257 A1 | 12/2010 | Aranyi | |
| 2010/0320254 A1 | 12/2010 | Zemlok et al. | |
| 2011/0034910 A1 | 2/2011 | Ross et al. | |
| 2011/0062211 A1 | 3/2011 | Ross et al. | |
| 2011/0168757 A1 | 7/2011 | Viola et al. | |
| 2011/0172681 A1 | 7/2011 | Aranyi et al. | |
| 2011/0190738 A1 | 8/2011 | Zemlok et al. | |
| 2011/0301579 A1 | 12/2011 | Marczyk et al. | |
| 2011/0303735 A1 | 12/2011 | Marczyk | |
| 2012/0055972 A1 | 3/2012 | Marczyk | |
| 2012/0074197 A1 | 3/2012 | Marczyk | |
| 2012/0175400 A1 | 7/2012 | Viola et al. | |
| 2012/0193393 A1 | 8/2012 | Viola et al. | |
| 2012/0198288 A1 | 8/2012 | Njo et al. | |
| 2012/0220989 A1 | 8/2012 | Zemlok et al. | |
| 2012/0223121 A1 | 9/2012 | Viola et al. | |
| 2012/0241494 A1 | 9/2012 | Marczyk | |
| 2012/0277790 A1 | 11/2012 | Zemlok et al. | |
| 2012/0298718 A1 | 11/2012 | Marczyk | |
| 2012/0298720 A1 | 11/2012 | Marczyk | |
| 2019/0183503 A1* | 6/2019 | Shelton, IV | A61B 90/06 |
| 2022/0331047 A1* | 10/2022 | Shelton, IV | G06F 3/011 |
| 2023/0051361 A1 | 2/2023 | Shelton, IV et al. | |
| 2023/0116571 A1 | 4/2023 | Shelton, IV et al. | |

FOREIGN PATENT DOCUMENTS

| | | |
|---|---|---|
| CN | 102648864 A | 8/2012 |
| EP | 0537570 A2 | 4/1993 |
| EP | 0647431 A2 | 4/1995 |
| EP | 0738501 A1 | 10/1996 |
| EP | 0770354 A1 | 5/1997 |
| EP | 1070487 A2 | 1/2001 |
| EP | 1201196 A1 | 5/2002 |
| EP | 1658817 A1 | 5/2006 |
| EP | 1813203 A2 | 8/2007 |
| FR | 2849589 A1 | 7/2004 |
| WO | 9414129 A1 | 6/1994 |
| WO | 9729694 A1 | 8/1997 |
| WO | 9740760 A1 | 11/1997 |
| WO | 9837825 A1 | 9/1998 |
| WO | 9952489 A1 | 10/1999 |
| WO | 0234140 A2 | 5/2002 |
| WO | 03026511 A1 | 4/2003 |
| WO | 03030743 A2 | 4/2003 |
| WO | 2004032760 A2 | 4/2004 |
| WO | 2007030753 A2 | 3/2007 |
| WO | 2007114868 A2 | 10/2007 |
| WO | 2007118179 A2 | 10/2007 |
| WO | 2007014355 A3 | 4/2009 |
| WO | 2009143092 A1 | 11/2009 |
| WO | 2019043508 A2 | 3/2019 |

OTHER PUBLICATIONS

Detemple, P., "Microtechnology in Modern Health Care", Med Device Technol. 9(9):18-25 (1998).
Abridged Data Sheet, "DeepCover Secure Authenticator with 1-Wire SHA-256 and 512-Bit User EEPROM", Maxim Integrated Products, Inc. pp 1-4; 42; Dec. 2012.
Data Sheet "DS28E15—1-Sire SHA-256 Secure Authenticator with 512-Bit User EEPROM" ; IC-ON-LINE, Electronic Component Manufacturers, pp. 1-2; Aug. 2013.

* cited by examiner

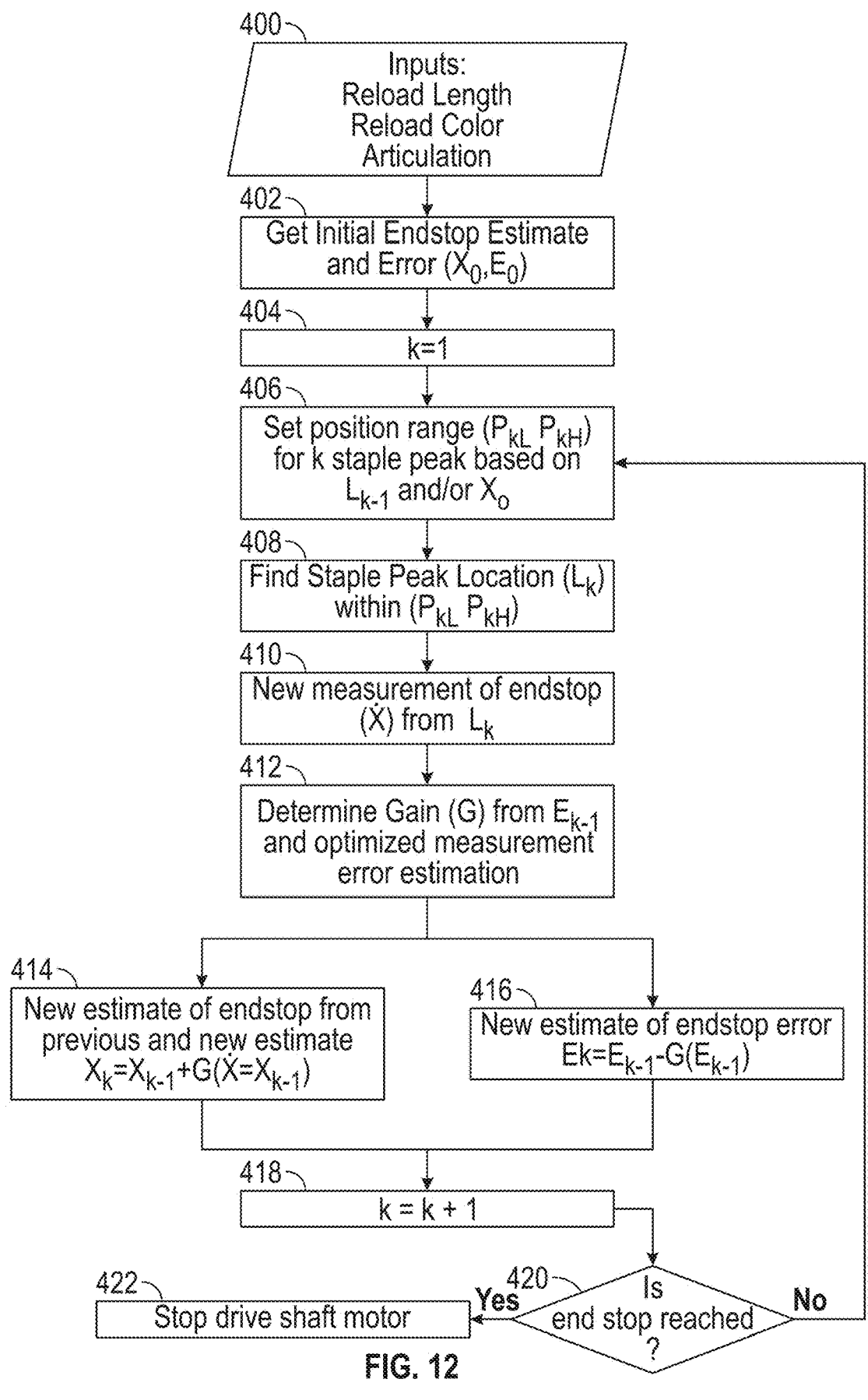

400
Inputs:
Reload Length
Reload Color
Articulation

402
Get Initial Endstop Estimate
and Error ($X_0$,$E_0$)

404
k=1

406
Set position range ($P_{kL}$ $P_{kH}$)
for k staple peak based on
$L_{k-1}$ and/or $X_o$ 408
Find Staple Peak Location ($L_k$)
within ($P_{kL}$ $P_{kH}$)

410
New measurement of endstop
($\dot{X}$) from $L_k$

412
Determine Gain (G) from $E_{k-1}$
and optimized measurement
error estimation 414
New estimate of endstop from
previous and new estimate
$X_k = X_{k-1} + G(\dot{X} = X_{k-1})$ 416
New estimate of endstop error
$Ek = E_{k-1} - G(E_{k-1})$ 418
k = k + 1

420
Is
end stop reached
?

Yes    No

422
Stop drive shaft motor

FIG. 12

ROBOTIC OR POWERED SURGICAL STAPLER WITH PREDICTIVE STAPLING END STOP

CROSS-REFERENCE TO RELATED APPLICATIONS

This application claims the benefit of, and priority to, U.S. Provisional Patent Application Ser. No. 63/590,814 filed on Oct. 17, 2023. The entire contents of the foregoing application are incorporated by reference herein.

BACKGROUND

Surgical robotic systems may include a surgeon console controlling one or more surgical robotic arms, each having a surgical instrument having an end effector. In operation, the robotic arm is moved to a position over a patient and the surgical instrument is guided into a small incision via a surgical access port or a natural orifice of a patient to position the end effector at a work site within the patient's body. The surgical instrument may be a surgical stapler having an articulatable end effector configured to clamp, fasten, and cut tissue. Such surgical staplers may also be powered handheld instruments. In powered handheld or robotic surgical staplers, a drive mechanism is advanced to approximate a pair of jaws of the end effector while simultaneously ejecting fasteners and cutting tissue.

Robotic and powered handheld surgical staplers may stop firing (e.g., advancing the drive mechanism) by sensing an increase in motor current caused when the mechanism in the end effector can no longer advance due to contacting an end stop, e.g., end of a travel channel in the end effector. This increase in motor current is caused by the rapid increase in mechanical strain developed in the stapler due to pressing against a mechanical limit. Reaching the mechanical limit with the drive mechanism causes an undesired motion (e.g., twitching) in the end effector whereby the articulation angle of the end effector is changed as a result of the increased force in the system.

SUMMARY

The present disclosure provides a stapling loading unit including an articulatable end effector having a pair of jaw members, e.g., anvil and staple cartridge, that are closed and opened by advancing and retracting a drive mechanism actuated by one or more motors. The loading unit, which may be a single use or reusable unit, may be attached, either directly or using an adapter, to a robotic surgical system or a powered handheld surgical instrument. The adapter, loading unit, and/or staple cartridge may include a storage device configured to store one or more parameters pertaining thereto (e.g., length of a stapling cartridge, maximum torque, etc.), which may be provided as a maximum torque and/or current and/or force, that is used by the robotic surgical system or powered handheld surgical instrument to operate its motor(s) to control operation of the loading unit during stapling. The storage device may also provide torque or current draw thresholds for detecting an initial peak and a distance offset for determining the end stop and controlling the motor(s) based on the same. The distance required to reach end stop varies based on a variety of factors, such as the articulation angle of the end effector and the tissue thickness, so stopping after a set distance may not be desired even if the staple cartridge length is known, i.e., provided in the data read from the storage device. Thus, using an offset added to a determined distance during the stapling process provides a more accurate estimation of the end stop.

The present disclosure provides a predictive algorithm, which may be embodied as software instructions stored in a non-transitory medium and executable by a processor. During a motor-powered actuation of the load unit (e.g., either in a powered handheld or robotic stapling system), one or more data signals are captured by the system, which may be analyzed in real time or after the firing. Data signals may include any motor parameter such as torque, speed, current, etc. as well as force or strain imparted on mechanical components of the loading unit, which may be measured via corresponding strain sensors.

The algorithm is based on identifying a pattern that correlates to actions that happen within the staple cartridge during firing. Total travel distance by a drive mechanism from the start of the stapling process to end stop varies based on articulation angle and tissue thickness. Thus, the start of the process and the corresponding data pattern also varies. However, once the pattern is detected, the remainder of the firing process, including end stop follows a predictable sequence. The algorithm may also use the data stored on the storage device including the length of the staple cartridge and a distance offset value. The algorithm identifies the pattern based on the length of the staple cartridge, i.e., early in the firing, and predicts the location of the end stop based on the known nature of the pattern. In predicting where end stop will occur for each firing process, the firing process is stopped before the rapid increase in force as a result of the knife bar or drive shaft hitting the end of the channel slot and therefore the undesired motion (e.g., twitching of the end effector) is minimized.

According to one embodiment of the present disclosure, a surgical robotic system is disclosed. The surgical robotic system includes a robotic arm having an instrument drive unit, which includes a motor and a sensor for measuring an actuation parameter. The system also includes a loading unit having an end effector, which includes a staple cartridge and an anvil, the staple cartridge having a plurality of staples and the anvil configured to form the plurality of staples upon firing. The loading unit also includes a drive shaft movable through the end effector for approximating one or both of the staple cartridge or the anvil relative to each other. The system further includes an adapter for coupling the loading unit to the instrument drive unit such that the motor actuates the drive shaft. The system further includes a controller for: receiving the actuation parameter and determining a first position of the drive shaft based on the measured parameter; calculating a stop position, based on the first position, for the drive shaft that occurs prior to reaching a mechanical limit of the drive shaft; and stopping the motor such that the drive shaft stops at the stop position.

Implementations of the above embodiment may include one or more of the following features. According to one aspect of the above embodiment, the sensor may be a motor torque sensor, a motor current sensor, or a strain sensor. The parameter may be motor torque, current draw, or strain. The controller may further calculate the stop position by adding an offset value to the first position. The instrument drive unit may further include a position sensor for measuring position of the motor. The loading unit may include a storage device storing a maximum threshold value and the offset value, the storage device being accessible by the controller. The controller may also determine the first position based on the position of the motor at a point in time when the parameter exceeds the maximum threshold.

According to another embodiment of the present disclosure, a powered surgical stapler is disclosed. The stapler includes a handle having a motor and a sensor for measuring an actuation parameter. The stapler also includes a loading unit having an end effector, which includes a staple cartridge and an anvil, the staple cartridge having a plurality of staples and the anvil configured to form the plurality of staples upon firing. The loading unit also includes a drive shaft movable through the end effector for approximating one or both of the staple cartridge or the anvil relative to each other. The stapler further includes an adapter for coupling the loading unit to the handle such that the motor actuates the drive shaft. The stapler additionally includes a controller for: receiving the actuation parameter and determining a first position of the drive shaft based on the measured parameter; calculating a stop position or potential stop positions, based on the first position, for the drive shaft that occurs prior to reaching a mechanical limit of the drive shaft; and stopping the motor such that the drive shaft stops at the stop position.

Implementations of the above embodiment may include one or more of the following features. According to one aspect of the above embodiment, the sensor may be a motor torque sensor, a motor current sensor, or a strain sensor. The parameter may be motor torque, current draw, or strain. The controller may further calculate the stop position by adding an offset value to the first position. The handle may further include a position sensor for measuring position of the motor. The loading unit may include a storage device storing a maximum threshold value and the offset value, the storage device being accessible by the controller. The controller may also determine the first position based on the position of the motor at a point in time when the parameter exceeds the maximum threshold.

According to a further embodiment of the present disclosure, a method for controlling a motor actuated surgical stapler is disclosed. The method includes activating, via a controller, a motor of an instrument drive unit coupled to a loading unit. The loading unit includes an end effector having a staple cartridge and an anvil, with the staple cartridge having a plurality of staples and the anvil being configured to form the plurality of staples upon firing. The loading unit also includes a drive shaft movable through the end effector for approximating one of the staple cartridge or the anvil relative to each other. The method may include measuring an actuation parameter at a sensor. The method also includes determining, at the controller, a first position of the drive shaft based on the measured parameter. The method further includes calculating, at the controller, a stop position, based on the first position, for the drive shaft that occurs prior to reaching a mechanical limit of the drive shaft. The method additionally includes stopping the motor such that the drive shaft stops at the stop position.

Implementations of the above embodiment may include one or more of the following features. According to one aspect of the above embodiment, the parameter may be motor torque, current draw, or strain. Calculating the stop position may further include adding an offset value to the first position. The method may also include measuring position of the motor at a position sensor. The method may further include reading, via the controller, from a storage device storing a maximum threshold value and the offset value. The first position may be determined based on the position of the motor at a point in time when the parameter exceeds the maximum threshold.

According to a further embodiment of the present disclosure, a system for controlling an end effector of a surgical stapling instrument is disclosed. The system includes a stapling instrument having an end effector with an anvil and a staple cartridge with a plurality of staples, where one or both of the anvil and the staple cartridge are movable relative to each other. The system also includes a drive shaft movable through the end effector to eject the plurality of staples. The system further includes a motor for actuating the drive shaft and a sensor configured to measure an actuation parameter associated with one of the drive shaft or the motor during ejection of the plurality of staples. The system additionally includes a controller configured to receive the actuation parameter from the sensor, detect multiple signal events corresponding to one of a peak or a valley in the actuation parameter, and estimate an end stop position for the drive shaft that occurs prior to reaching a mechanical limit of the drive shaft based on a signal event. The controller is further configured to continuously update the estimated end stop position based on subsequent signal events, determine a final end stop position based the estimated end stop position before the drive shaft reaches a mechanical limit, and generate a stop command to stop the motor when the final end stop position is reached.

Implementations of the above embodiment may include one or more of the following features. According to one aspect of the above embodiment, the signal events may be caused by staple ejections. The drive shaft may be further configured to approximate at least one of the anvil or the staple cartridge relative to each other. The controller may be further configured to use a sequential Kalman filtering process. The controller may be also configured to calculate an error between a prior estimated end stop position and a current estimated end stop position. The controller may be additionally configured to calculate a gain value and update the estimated end stop position by adding a gain multiplied difference between the prior estimated end stop position and the current estimated end stop position to the current estimated end stop.

BRIEF DESCRIPTION OF THE DRAWINGS

Various embodiments of the present disclosure are described herein with reference to the drawings wherein:

FIG. 12 is a flow chart of another method for controlling the surgical instrument of FIG. 5.

DETAILED DESCRIPTION

Figure 1:
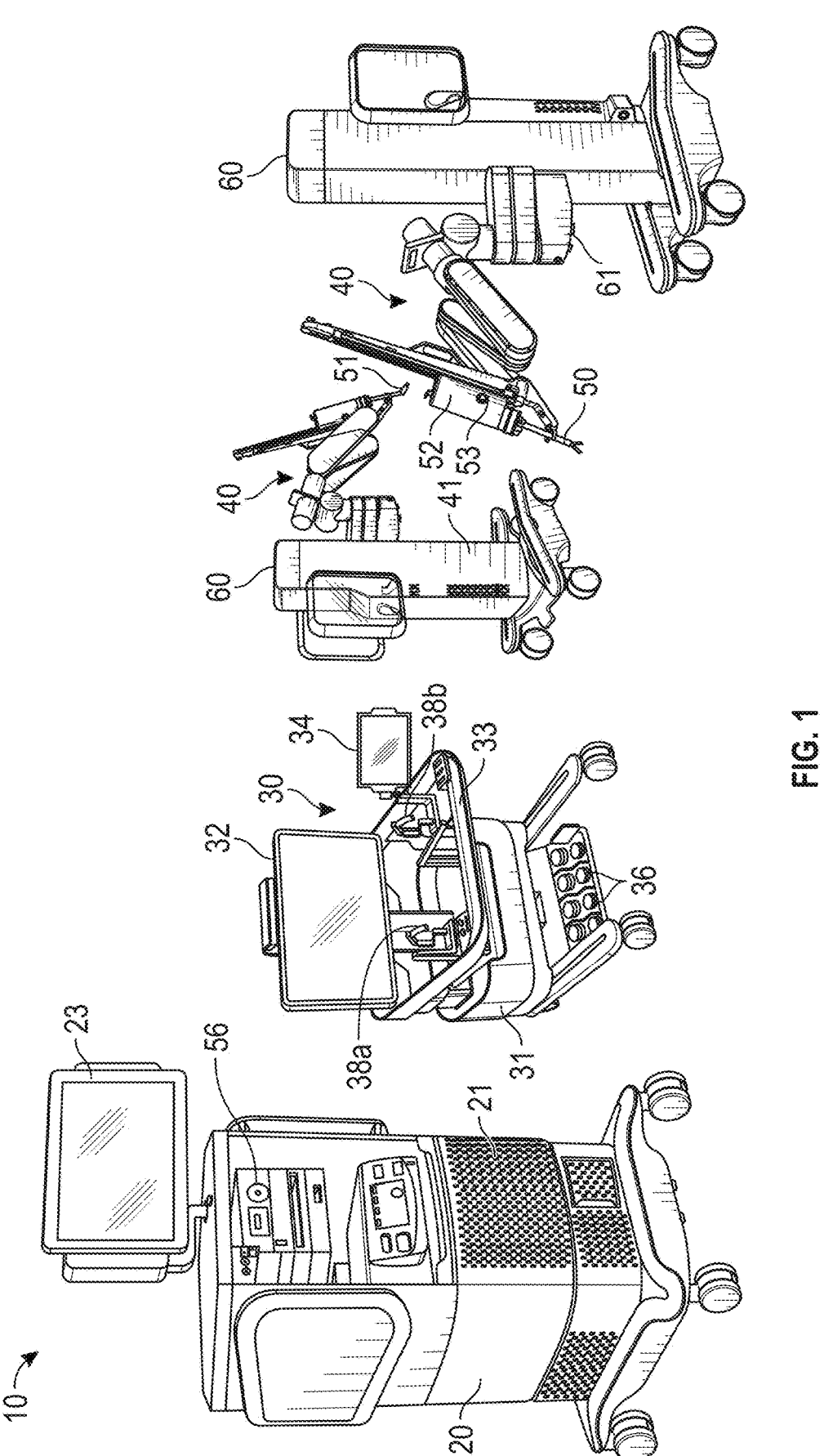
FIG. 1 is a perspective illustration of a surgical robotic system including a control tower, a console, and one or more surgical robotic arms each disposed on a mobile cart according to an embodiment of the present disclosure.

Embodiments of the presently disclosed surgical stapling systems are described in detail with reference to the drawings, in which like reference numerals designate identical or corresponding elements in each of the several views. As used herein the term "proximal" refers to the portion of the surgical robotic system and/or the surgical instrument coupled thereto that is closer to a base of a robot, while the term "distal" refers to the portion that is farther from the base of the robot.

As will be described in detail below, in aspects, the present disclosure is directed to a surgical robotic system, which includes a surgeon console, a control tower, and one or more mobile carts having a surgical robotic arm coupled to a setup arm. The surgeon console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

With reference to FIG. 1, a surgical robotic system 10 includes a control tower 20, which is connected to all of the components of the surgical robotic system 10 including a surgeon console 30 and one or more movable carts 60. Each of the movable carts 60 includes a robotic arm 40 having a surgical instrument 50 removably coupled thereto. The robotic arm 40 is also coupled to the movable cart 60. The robotic system 10 may include any number of movable carts 60 and/or robotic arms 40.

The surgical instrument 50 is configured for use during minimally invasive surgical procedures. In embodiments, the surgical instrument 50 may be configured for open surgical procedures. In embodiments, the surgical instrument 50 may be an endoscope, such as an endoscopic camera 51, configured to provide a video feed for the user. In further embodiments, the surgical instrument 50 may be an electrosurgical forceps configured to seal tissue by compressing tissue between jaw members and applying electrosurgical current thereto. In yet further embodiments, the surgical instrument 50 may be a surgical stapler including a pair of jaws configured to grasp and clamp tissue while deploying a plurality of tissue fasteners, e.g., staples, and cutting stapled tissue.

One of the robotic arms 40 may include the endoscopic camera 51 configured to capture video of the surgical site. The endoscopic camera 51 may be a stereoscopic endoscope configured to capture two side-by-side (i.e., left and right) images of the surgical site to produce a video stream of the surgical scene. The endoscopic camera 51 is coupled to a video processing device 56, which may be disposed within the control tower 20. The video processing device 56 may be any computing device as described below configured to receive the video feed from the endoscopic camera 51 perform the image processing based on the depth estimating algorithms of the present disclosure and output the processed video stream.

The surgeon console 30 includes a first display 32, which displays a video feed of the surgical site provided by camera 51 of the surgical instrument 50 disposed on the robotic arms 40, and a second display 34, which displays a user interface for controlling the surgical robotic system 10. The first and second displays 32 and 34 are touchscreens allowing for displaying various graphical user inputs.

The surgeon console 30 also includes a plurality of user interface devices, such as foot pedals 36 and a pair of handle controllers 38a and 38b which are used by a user to remotely control robotic arms 40. The surgeon console further includes an armrest 33 used to support clinician's arms while operating the handle controllers 38a and 38b.

The control tower 20 includes a display 23, which may be a touchscreen, and outputs on the graphical user interfaces (GUIs). The control tower 20 also acts as an interface between the surgeon console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgeon console 30, in such a way that robotic arms 40 and the surgical instrument 50 execute a desired movement sequence in response to input from the foot pedals 36 and the handle controllers 38a and 38b.

Each of the control tower 20, the surgeon console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area network, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
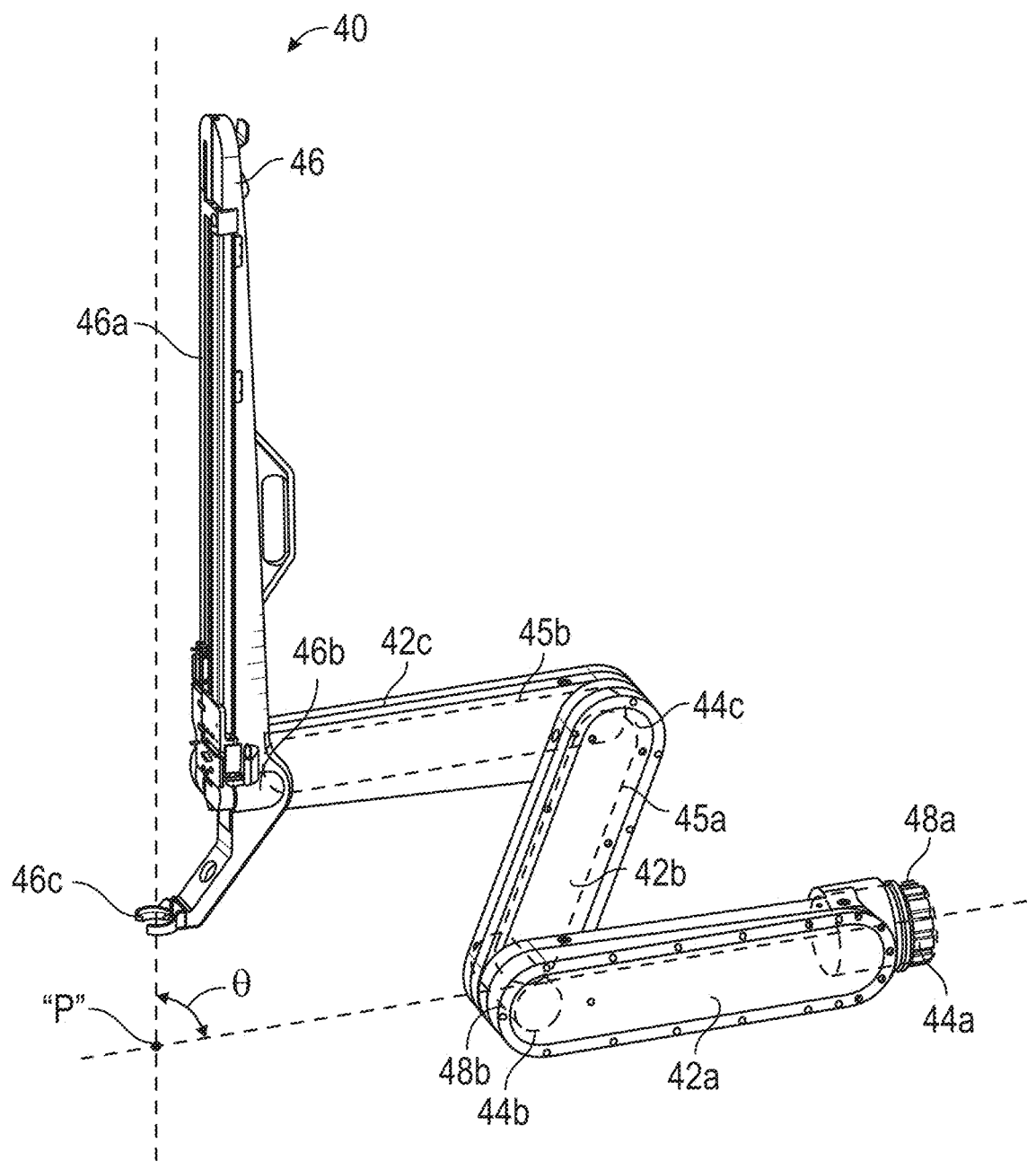
FIG. 2 is a perspective view of a surgical robotic arm of the surgical robotic system of FIG. 1 according to an embodiment of the present disclosure.
Figure 3:
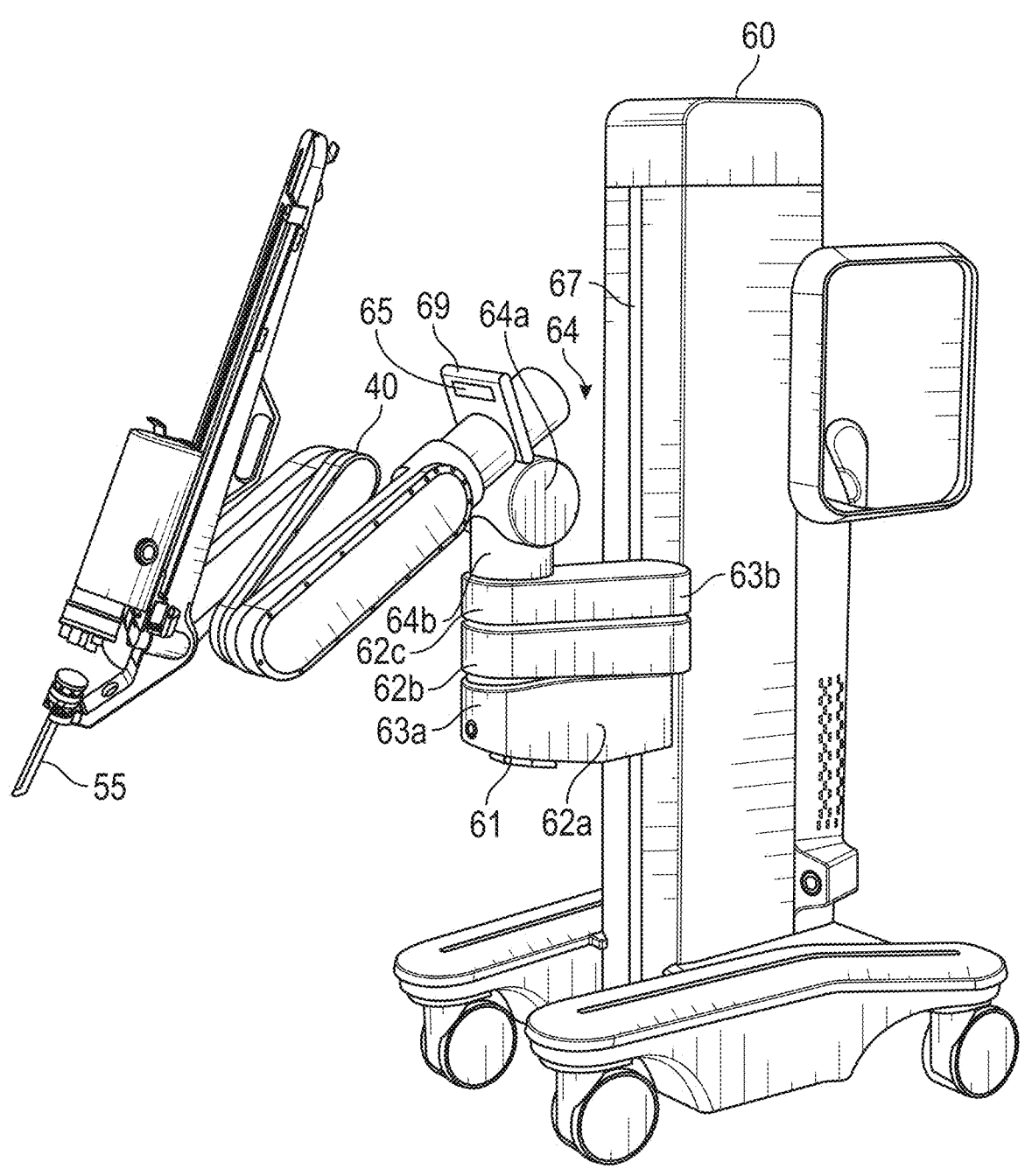
FIG. 3 is a perspective view of a setup arm with the surgical robotic arm of the surgical robotic system of FIG. 1 according to an embodiment of the present disclosure.

With reference to FIG. 2, each of the robotic arms 40 may include a plurality of links 42a, 42b, 42c, which are inter-connected at joints 44a, 44b, 44c, respectively. Other con-figurations of links and joints may be utilized as known by those skilled in the art. The joint 44a is configured to secure the robotic arm 40 to the mobile cart 60 and defines a first longitudinal axis. With reference to FIG. 3, the mobile cart 60 includes a lift 67 and a setup arm 61, which provides a base for mounting of the robotic arm 40. The lift 67 allows for vertical movement of the setup arm 61. The mobile cart 60 also includes a display 69 for displaying information pertaining to the robotic arm 40. In embodiments, the robotic arm 40 may include any type and/or number of joints.

The setup arm 61 includes a first link 62a, a second link 62b, and a third link 62c, which provide for lateral maneu-verability of the robotic arm 40. The links 62a, 62b, 62c are interconnected at joints 63a and 63b, each of which may include an actuator (not shown) for rotating the links 62b and 62b relative to each other and the link 62c. In particular, the links 62a, 62b, 62c are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 61 may include controls (not shown) for adjusting movement of the links 62a, 62b, 62c as well as the lift 67. In embodiments, the setup arm 61 may include any type and/or number of joints.

The third link 62c may include a rotatable base 64 having two degrees of freedom. In particular, the rotatable base 64 includes a first actuator 64a and a second actuator 64b. The first actuator 64a is rotatable about a first stationary arm axis which is perpendicular to a plane defined by the third link 62c and the second actuator 64b is rotatable about a second stationary arm axis which is transverse to the first stationary arm axis. The first and second actuators 64a and 64b allow for full three-dimensional orientation of the robotic arm 40.

The actuator 48b of the joint 44b is coupled to the joint 44c via the belt 45a, and the joint 44c is in turn coupled to the joint 46b via the belt 45b. Joint 44c may include a transfer case coupling the belts 45a and 45b, such that the actuator 48b is configured to rotate each of the links 42b, 42c and a holder 46 relative to each other. More specifically, links 42b, 42c, and the holder 46 are passively coupled to the actuator 48b which enforces rotation about a pivot point "P" which lies at an intersection of the first axis defined by the link 42a and the second axis defined by the holder 46. In other words, the pivot point "P" is a remote center of motion (RCM) for the robotic arm 40. Thus, the actuator 48b controls the angle θ between the first and second axes allowing for orientation of the surgical instrument 50. Due to the interlinking of the links 42a, 42b, 42c, and the holder 46 via the belts 45a and 45b, the angles between the links 42a, 42b, 42c, and the holder 46 are also adjusted in order to achieve the desired angle θ. In embodiments, some or all of the joints 44a, 44b, 44c may include an actuator to obviate the need for mechanical linkages.

The joints 44a and 44b include an actuator 48a and 48b configured to drive the joints 44a, 44b, 44c relative to each other through a series of belts 45a and 45b or other mechani-cal linkages such as a drive rod, a cable, or a lever and the like. In particular, the actuator 48a is configured to rotate the robotic arm 40 about a longitudinal axis defined by the link 42a.

With reference to FIG. 2, the holder 46 defines a second longitudinal axis and is configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components (e.g., end effector) of the surgical instrument 50. The holder 46 includes a sliding mechanism 46a, which is configured to move the IDU 52 along the second longitudinal axis defined by the holder 46. The holder 46 also includes a joint 46b, which rotates the holder 46 relative to the link 42c. During endoscopic pro-cedures, the instrument 50 may be inserted through an endoscopic port 55 (FIG. 3) held by the holder 46. The holder 46 also includes a port latch 46c for securing the port 55 to the holder 46 (FIG. 2).

The robotic arm 40 also includes a plurality of manual override buttons 53 (FIG. 1) disposed on the IDU 52 and the setup arm 61, which may be used in a manual mode. The user may press one or more of the buttons 53 to move the component associated with the button 53.

Figure 4:
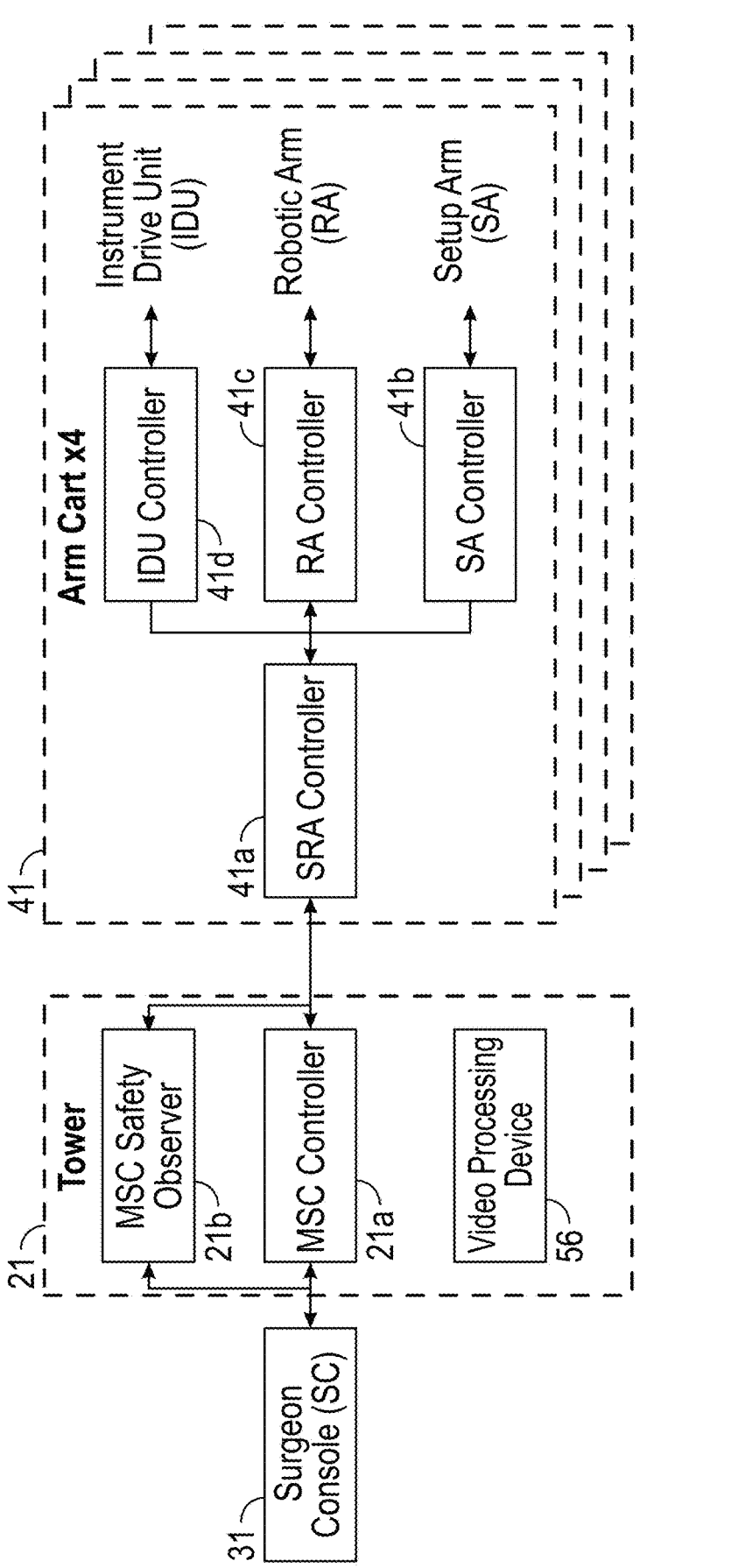
FIG. 4 is a schematic diagram of a computer architecture of the surgical robotic system of FIG. 1 according to an embodiment of the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21a and safety observer 21b. The controller 21a receives data from the computer 31 of the surgeon console 30 about the current position and/or orientation of the handle controllers 38a and 38b and the state of the foot pedals 36 and other buttons. The controller 21a processes these input positions to determine desired drive commands for each joint of the robotic arm 40 and/or the IDU 52 and commu-nicates these to the computer 41 of the robotic arm 40. The controller 21a also receives the actual joint angles measured by encoders of the actuators 48a and 48b and uses this information to determine force feedback commands that are transmitted back to the computer 31 of the surgeon console 30 to provide haptic feedback through the handle controllers 38a and 38b. The safety observer 21b performs validity checks on the data going into and out of the controller 21a and notifies a system fault handler if errors in the data transmission are detected to place the computer 21 and/or the surgical robotic system 10 into a safe state.

The computer 41 includes a plurality of controllers, namely, a main cart controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the mobile cart 60, the robotic arm 40, and the IDU 52. The main cart controller 41a also communicates actual joint angles back to the controller 21a.

Each of joints 63a and 63b and the rotatable base 64 of the setup arm 61 are passive joints (i.e., no actuators are present therein) allowing for manual adjustment thereof by a user. The joints 63a and 63b and the rotatable base 64 include brakes that are disengaged by the user to configure the setup arm 61. The setup arm controller 41b monitors slippage of each of joints 63a and 63b and the rotatable base 64 of the setup arm 61, when brakes are engaged or can be freely moved by the operator when brakes are disengaged, but do not impact controls of other joints. The robotic arm control-ler 41c controls each joint 44a and 44b of the robotic arm 40 and calculates desired motor torques required for gravity compensation, friction compensation, and closed loop position control of the robotic arm 40. The robotic arm controller 41c calculates a movement command based on the calculated torque. The calculated motor commands are then communicated to one or more of the actuators 48a and 48b in the robotic arm 40. The actual joint positions are then transmitted by the actuators 48a and 48b back to the robotic arm controller 41c.

The IDU controller 41d receives desired joint angles for the surgical instrument 50, such as wrist and jaw angles, and computes desired currents for the motors in the IDU 52. The IDU controller 41d calculates actual angles based on the motor positions and transmits the actual angles back to the main cart controller 41a.

The robotic arm 40 is controlled in response to a pose of the handle controller controlling the robotic arm 40, e.g., the handle controller 38a, which is transformed into a desired pose of the robotic arm 40 through a hand eye transform function executed by the controller 21a. The hand eye function, as well as other functions described herein, is/are embodied in software executable by the controller 21a or any other suitable controller described herein. The pose of one of the handle controller 38a may be embodied as a coordinate position and role-pitch-yaw (RPY) orientation relative to a coordinate reference frame, which is fixed to the surgical console 30. The desired pose of the instrument 50 is relative to a fixed frame on the robotic arm 40. The pose of the handle controller 38a is then scaled by a scaling function executed by the controller 21a. In embodiments, the coordinate position may be scaled down and the orientation may be scaled up by the scaling function. In addition, the controller 21a may also execute a clutching function, which disengages the handle controller 38a from the robotic arm 40. In particular, the controller 21a stops transmitting movement commands from the handle controller 38a to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38a and is then passed by an inverse kinematics function executed by the controller 21a. The inverse kinematics function calculates angles for the joints 44a, 44b, 44c of the robotic arm 40 that achieve the scaled and adjusted pose input by the handle controller 38a. The calculated angles are then passed to the robotic arm controller 41c, which includes a joint axis controller having a proportional-derivative (PD) controller, the friction estimator module, the gravity compensator module, and a two-sided saturation block, which is configured to limit the commanded torque of the motors of the joints 44a, 44b, 44c.

Figure 5:
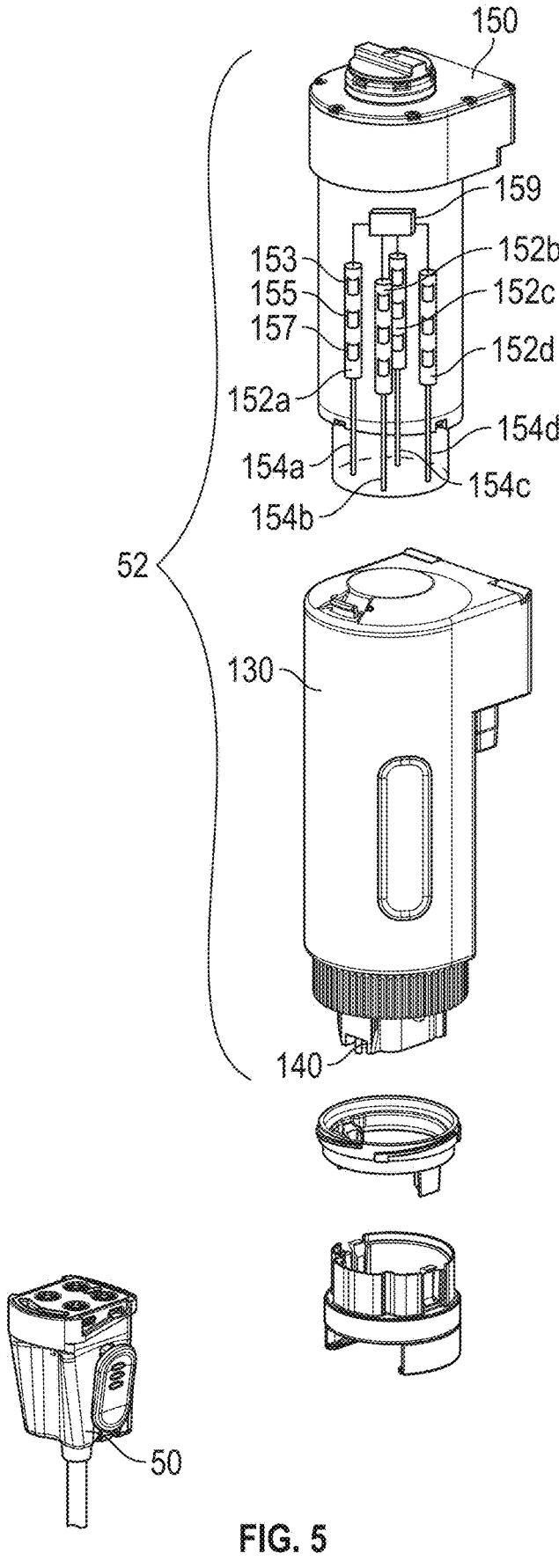
FIG. 5 is a perspective view, with parts separated, of the instrument drive unit and a surgical instrument according to an embodiment of the present disclosure.

With reference to FIG. 5, the IDU 52 is shown in more detail and is configured to transfer power and actuation forces from its motors 152a-d to the instrument 50 to drive movement of components of the instrument 50, such as articulation, rotation, pitch, yaw, clamping, cutting, etc. The IDU 52 may also be configured for the activation or firing of an electrosurgical energy-based instrument or the like (e.g., cable drives, pulleys, friction wheels, rack and pinion arrangements, etc.).

The IDU 52 includes a motor pack 150 and a sterile barrier housing 130. Motor pack 150 includes motors 152a-d for controlling various operations of the instrument 50. The instrument 50 is removably couplable to IDU 52. As the motors 152a-d of the motor pack 150 are actuated, rotation of the drive transfer shafts 154a, 154b, 154c, 154d of the motors 152a-d, respectively, is transferred to the drive assemblies of the instrument 50.

Figure 7:
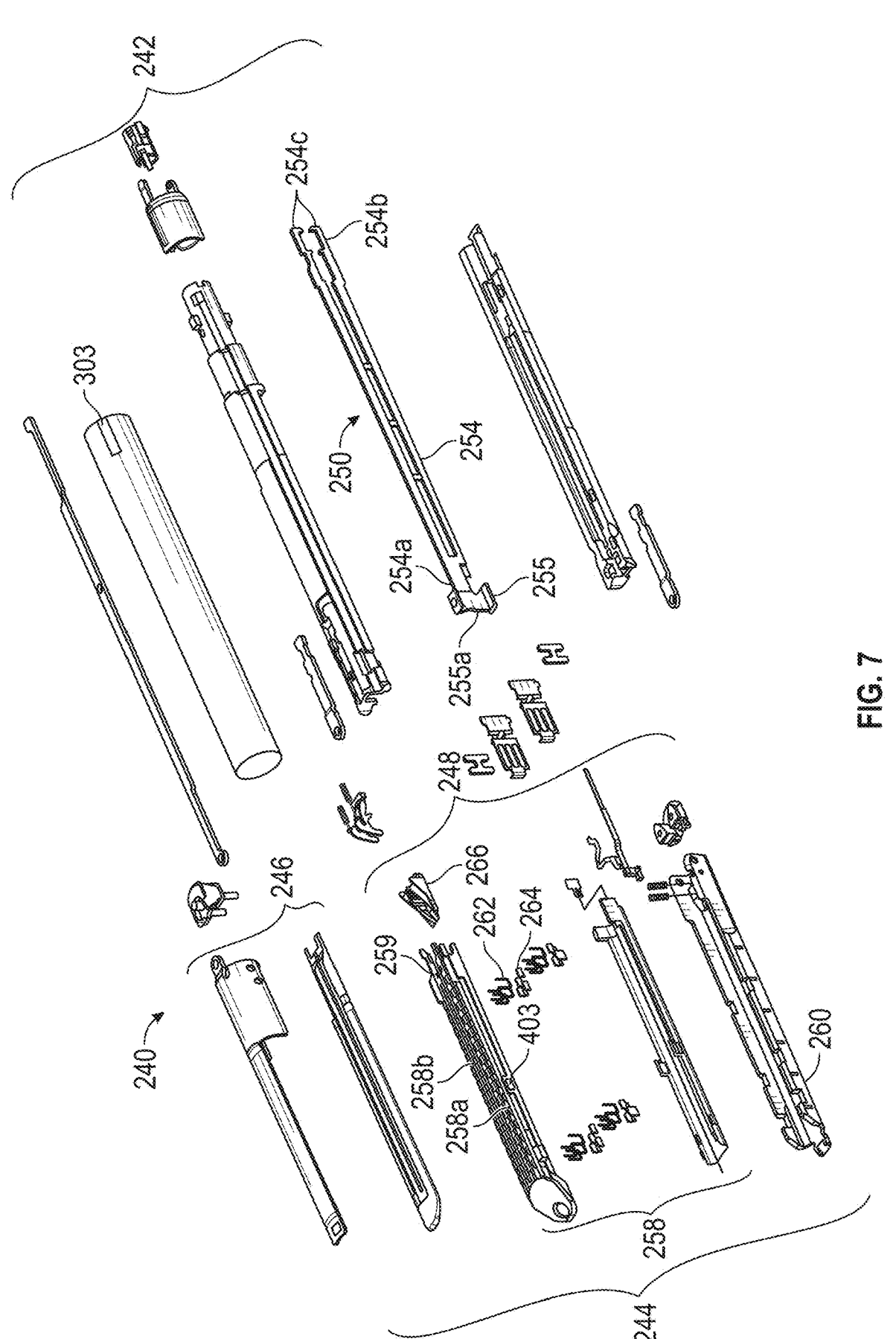
FIG. 7 is an enlarged, perspective view of a stapling end effector of the surgical instrument of FIG. 5 in an unarticulated position.

The instrument 50 is configured to couple to a loading unit 240 secured to a distal end thereof. The instrument 50 is configured to transfer rotational forces/movement supplied by the IDU 52 (e.g., via the motors 152a-d of the motor pack 150) into longitudinal movement or translation of the cables or drive shafts to effect various functions of an end effector 244 (FIG. 7).

Each of the motors 152a-d includes a current sensor 153, a torque sensor 155, and a position sensor 157, which may be an encoder configured to measure angular or linear position of the motor. For conciseness only operation of the motor 152a is described below. The sensors 153, 155, 157 monitor the performance of the motor 152a. The current sensor 153 is configured to measure the current draw of the motor 152a and the torque sensor 155 is configured to measure motor torque. The torque sensor 155 may be any force or strain sensor including one or more strain gauges configured to convert mechanical forces and/or strain into a sensor signal indicative of the torque output by the motor 152a. The sensor 157 may be any device that provides a sensor signal indicative of the number of rotations of the motor 152a, such as a mechanical encoder or an optical encoder. Parameters which are measured and/or determined by the sensor 157 may include speed, distance, revolutions per minute, position, and the like. The sensor signals from sensors 153, 155, 157 are transmitted to the IDU controller 41d, which then controls the motors 152a-d based on the sensor signals. In particular, the motors 152a-d are controlled by an actuator controller 159, which controls torque outputted and angular velocity of the motors 152a-d. In embodiments, additional position sensors may also be used, which include, but are not limited to, potentiometers coupled to movable components and configured to detect travel distances, Hall Effect sensors, accelerometers, and gyroscopes. In embodiments, a single controller can perform the functionality of the IDU controller 41d and the actuator controller 159.

Figure 6:
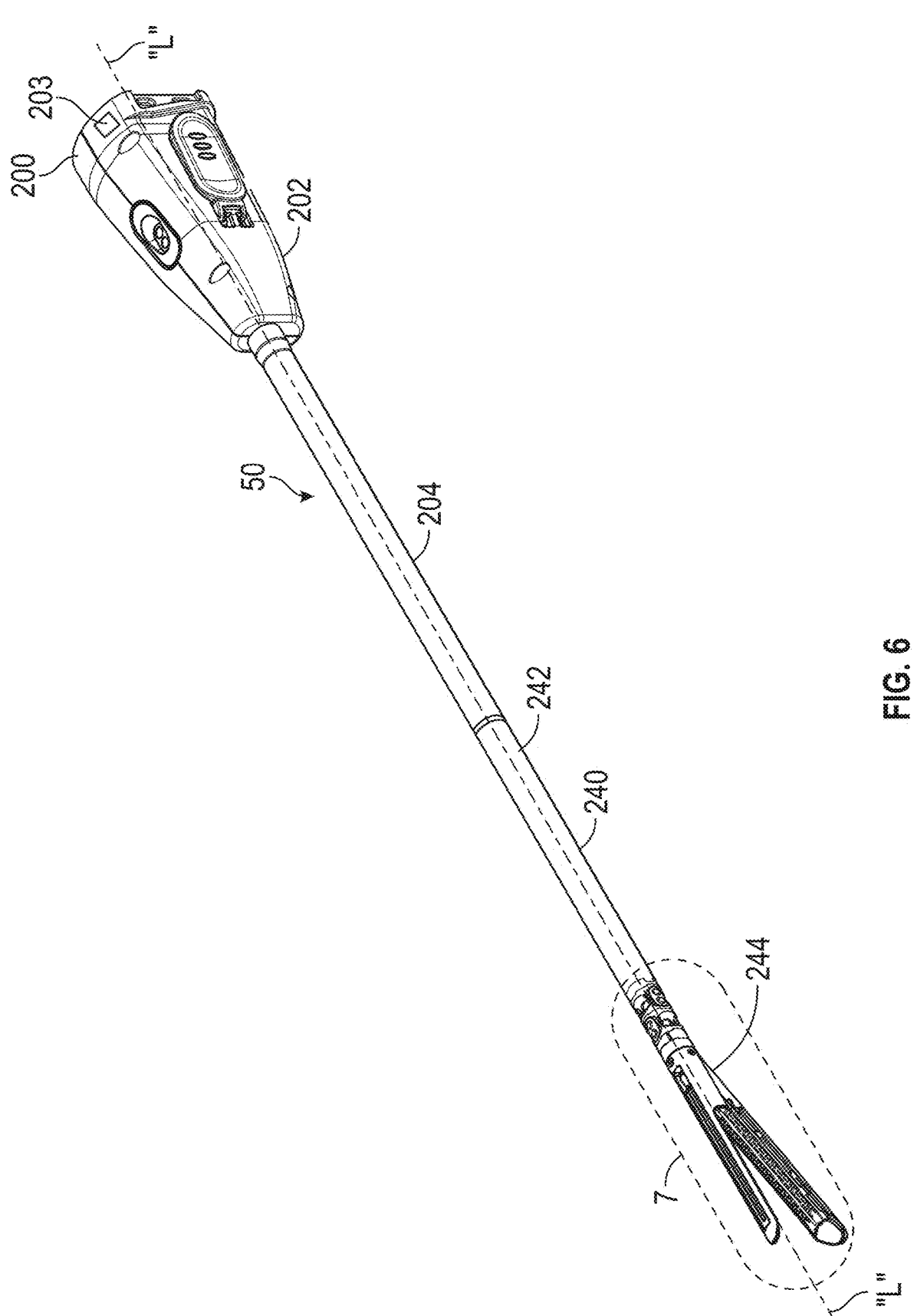
FIG. 6 is a perspective view of the surgical instrument of FIG. 5 in an unarticulated position.

With reference to FIG. 6, instrument 50 includes an adapter 200 having a housing 202 at a proximal end portion thereof and an elongated shaft 204 that extends distally from housing 202. Housing 202 of adapter 200 is configured to selectively couple to IDU 52, to enable motors 152a-d of IDU 52 to operate the loading unit 240 coupled to the instrument 50. Housing 202 of adapter 200 supports a drive assembly that mechanically and/or electrically cooperates with motors 152a-d of IDU 52. Drive assembly 250 of instrument 50 may include any suitable electrical and/or mechanical component to effectuate driving force/movement.

Elongated shaft 204 is configured to couple to the loading unit 240 having an end effector 244. With reference to FIGS. 6 and 7, the loading unit 240 includes a proximal body portion 242 and the end effector 244. Proximal body portion 242 is releasably attached to a distal end portion of the instrument 50, and end effector 244 is pivotally attached to a distal end of proximal body portion 242. End effector 244 includes an anvil assembly 246 and a cartridge assembly 248. Anvil assembly 246 is pivotable in relation to the cartridge assembly 248 and is movable between an open or unclamped position and a closed or clamped position. Proximal body portion 242 includes a drive assembly 250.

Drive assembly 250 includes a drive shaft 254, which may be flexible, and having a distal end portion 254a and a proximal engagement section 254b. The distal end portion 254a includes an I-beam 255 having a knife 255a. The I-beam 255 is configured to travel through the anvil assembly 246 and the cartridge assembly 248, thereby pushing the anvil assembly 246 toward the cartridge assembly 248 to clamp tissue. The proximal engagement section 254*b* includes diametrically opposed inwardly extending fingers 254*c* that engage a drive member (not shown) of the instrument 50 to fixedly secure drive member to the proximal end of flexible drive shaft 254. Drive member is actuated by the IDU 52.

Cartridge assembly 248 of end effector 244 includes a staple cartridge 258 removably supported in a carrier 260. Staple cartridge 258 defines a central longitudinal slot 258*a*, and a plurality of linear rows of staple retention slots 258*b* positioned on each side of the central longitudinal slot 258*a*. Each of the staple retention slots 258*b* receives a staple 262 and a portion of a staple pusher 264. During operation, drive assembly 250 abuts an actuation sled 266 and pushes actuation sled 266 through the staple cartridge 258. As the actuation sled 266 moves through staple cartridge 258, cam wedges of the actuation sled 266 sequentially engage staple pushers 264 to move staple pushers 264 vertically within staple retention slots 258*b* and sequentially eject the staples 262 therefrom for formation against an anvil plate 246*a* of anvil assembly 246. In addition, the drive shaft 254 closes the anvil assembly 246 and the cartridge assembly 248 and simultaneously advances the knife 255*a* and the actuation sled 266. Once clamping, cutting, and stapling is completed, the drive shaft 254 is retracted in a reverse (i.e., proximal) direction.

The adapter 200 includes a storage device 203 configured to store various operating parameters pertaining to the adapter 200. The IDU controller 41*d* may obtain the parameters automatically by reading the parameters from the storage device 203 and/or the parameters may be set manually by the user by selecting either the type of the adapter 200 and/or the loading unit 240. The storage device 203 may be any suitable device configured to store data, e.g., flash memory. The adapter 200 may also include a torque or force sensor (not shown) in addition or in lieu of the torque sensors 155 of the IDU 52.

The loading unit 240 may also include a storage device 303 (FIG. 7) configured to store various operating parameters pertaining to the loading unit 240. Such parameters may include, for example, a maximum torque and/or maximum current that may be used during retraction of the drive shaft 254 to open anvil assembly 246 and the cartridge assembly 248 to release stapled and cut tissue. Additional parameters may include staple cartridge 258 length, staple size, number of staples, and/or an articulation state. The handle may further include a position sensor for measuring a position of the motor. The storage device 303 may store a maximum a threshold value and the offset value, the storage device 303 being accessible by the controller. The storage device 303 may be connected to the IDU controller 41*d* using a wireless or a wired connection enabling for communication therebetween. The IDU controller 41*d* may obtain the parameters automatically by reading the parameters from the storage device 303 and/or the parameters may be set manually by the user by selecting either the type of the adapter 200 and/or the loading unit 240. The storage device 303 may be substantially similar to the storage device 203 and may be any suitable device configured to store data, e.g., flash memory.

In embodiments, the staple cartridge 258 may be removable from the loading unit 240, which itself may be removable or formed as part of the adapter 200. In this embodiment, a storage device 403, which is substantially similar to the storage devices 203 and 303, is configured to store various operating parameters pertaining the staple cartridge 258, such as staple cartridge 258 length, staple size, number of staples, etc. The staple cartridge 258 may be inserted into the carrier 260.

Figure 8:
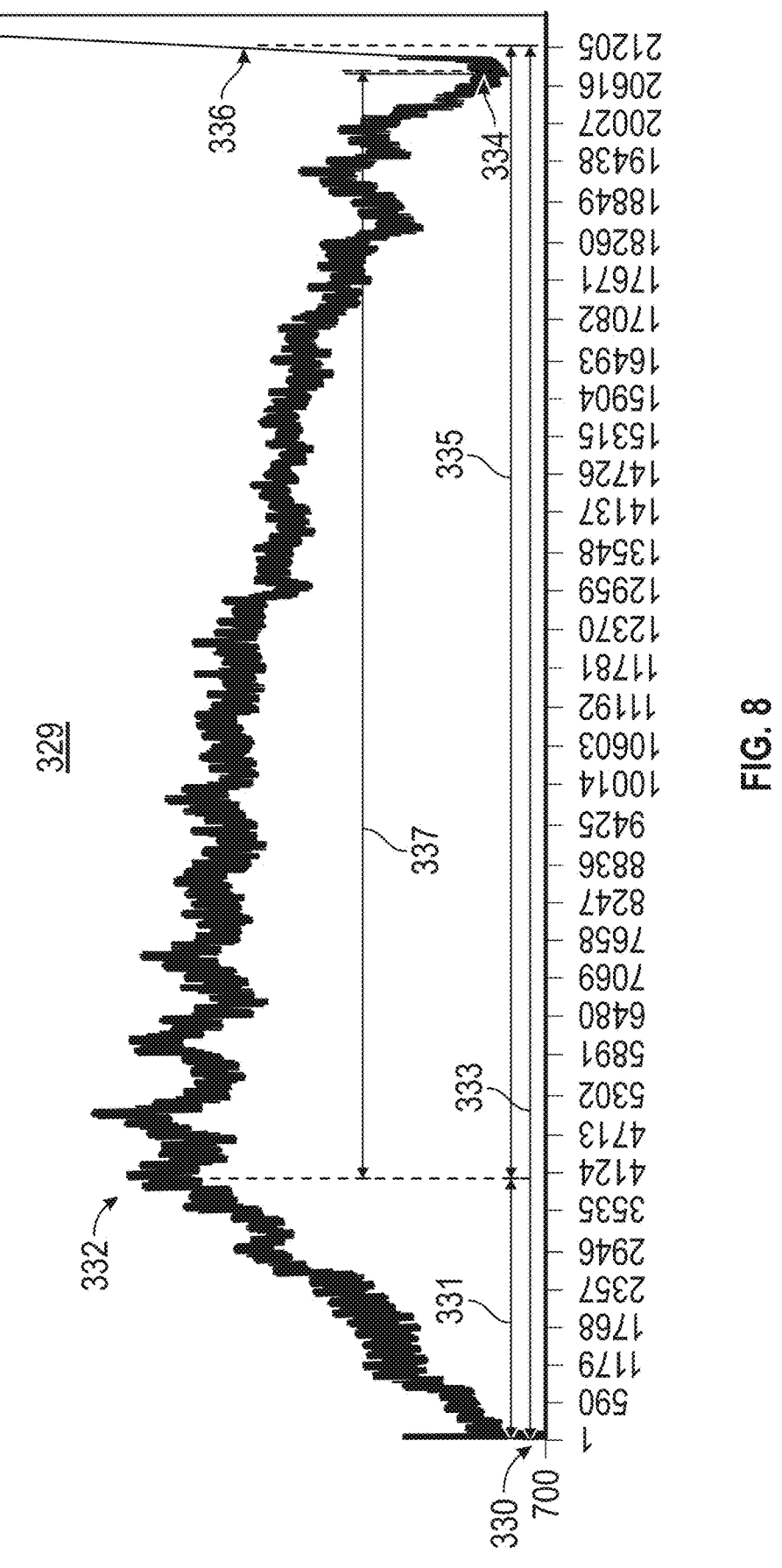
FIG. 8 is a measured signal plot of current draw over time generated by a controller based on current draw sensor according to an embodiment of the present disclosure.

FIG. 8 shows a plot 329 of a motor parameter, such as torque or current, during advancement of the drive shaft 254, i.e., simultaneous clamping, staple firing, and cutting process. Either motor torque or current may be used as these parameters provide similar data on motor operation during firing, that when plotted over time shows a similar plot. In addition to or as an alternative to using a motor parameter, any actuation parameter (e.g., force) may be used to generate the plot 329 and as a feedback parameter using the method of FIG. 9. Actuation parameter may be measured using a force or strain sensor that is in mechanical contact with any portion of the firing mechanism, such as strain gauge 160*b* of FIG. 11.

The plot 329 varies based on articulation angle and tissue thickness. The articulation angle refers to the angle between the proximal body portion 242 and the end effector 244 as the end effector 244 is articulated relative to the body portion 242 about a pivot point 243 via an articulation link 245 as shown in FIG. 7. During articulation, the longitudinal movement of the articulation link 245 articulated the end effector 244, which results in bending of the drive shaft 254 as the drive shaft 254 is advanced through the staple cartridge 258 and the anvil assembly 246.

With reference to FIG. 8, a first segment 331 and a second segment 333 of the plot 329 vary based on the articulation angle and tissue thickness. The first segment 331 is defined by a first point 330, which corresponds a start of firing process (i.e., the drive shaft 254 contacting the actuation sled 266), and a second point 332, which corresponds to a first peak of a motor parameter (i.e., the actuation sled 266 ejecting first row of staples). The second segment 333 is defined by the first point 330 and a third point 336, which corresponds to the end stop of the drive shaft 254 reaching its mechanical limit, which may be due to reaching end of channel of the staple cartridge 258 and/or the anvil assembly 246, a mechanical stop on a proximal portion of the drive shaft 254, or any other obstruction intended to stop travel of the drive shaft 254.

These first and second segments 331 and 333 are affected by the dimensions of the stapling adapter 200 and the loading unit 240. These dimensions are biased proximally or distally according to the forces of firing and articulation. However, a third segment 335 from the second point 332 to the third point 336 is fixed because the first peak of the motor parameter and the end stop are both caused by features within the staple cartridge 258 which has fixed dimensions. The present disclosure provides an algorithm that senses when the first peak has occurred and as a result accurately predicts when to stop, without reaching or detecting the mechanical limit. In particular, an offset is used to calculate the point at which motors are stopped without reaching the third point 336 (i.e., the end stop). The offset corresponds to a fourth segment 337, which is defined between the second point 332 and a fourth point 334, which corresponds to the end of staple ejections. In another embodiment, the algorithm may be configured to detect any peak to determine when the end stop will occur as described in further detail with respect to FIG. 12.

Figure 9:
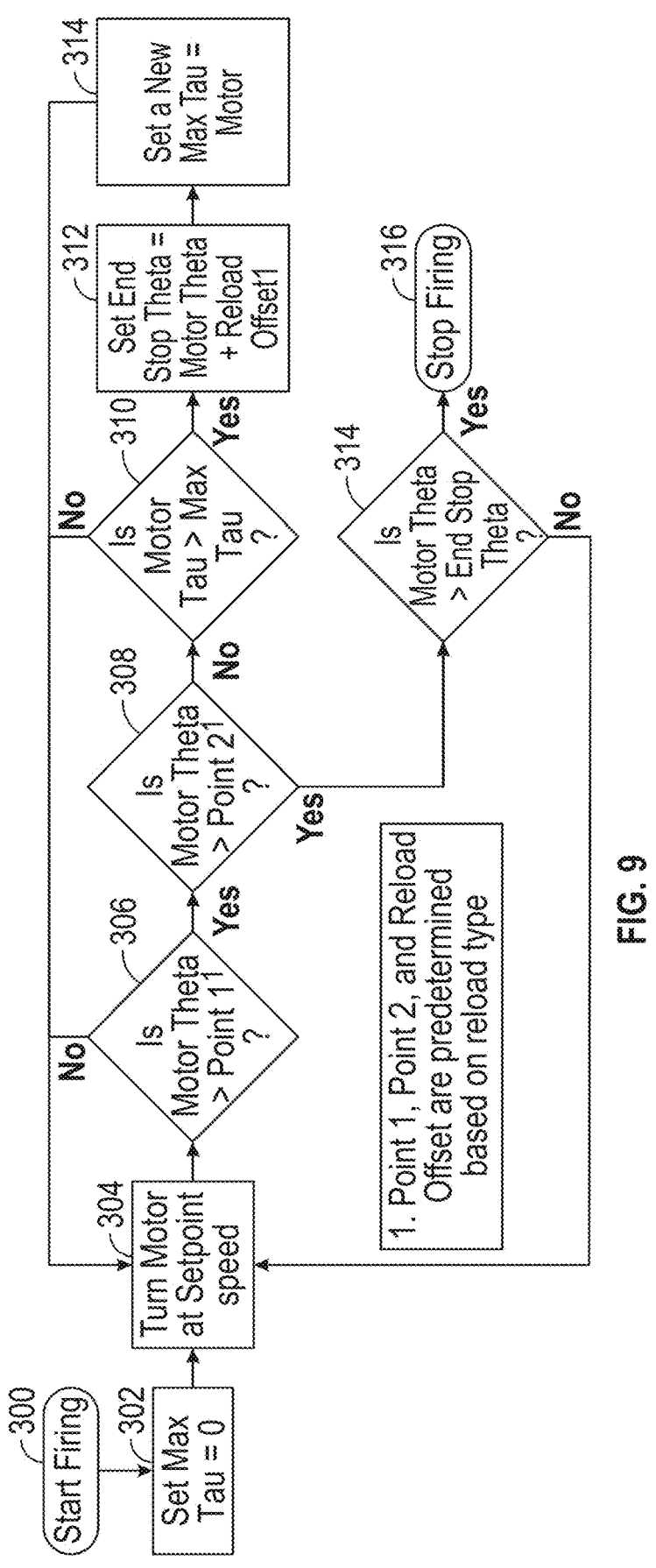
FIG. 9 is a flow chart of a method for controlling the surgical instrument of FIG. 5.

With reference to FIG. 9, an algorithm according to the present disclosure for controlling operation of a robotic or powered stapler is disclosed. The algorithm may be embodied as software instructions stored in a non-transitory computer readable medium and executable by a processor. The algorithm is shown as a flow chart of a method and includes at step 300 starting the firing process by pressing a button or trigger on the handle controller 38a or 38b and or one of the foot pedals 36. The method of FIG. 9 is described based on motor torque, however, any actuation parameter and corresponding sensor may be used, such as a current draw sensor or a force or strain sensor that is in mechanical contact with any portion of the firing mechanism, such as the strain gauge 160b of FIG. 11.

At step 302, the IDU controller 41d sets a maximum torque threshold to a 0 torque value. The threshold may be received from the storage device 203 or any other source, e.g., server, memory, etc. At step 304, one or more of the motors 152a-d are activated to advance the drive shaft 254, which closes the anvil assembly 246 and the cartridge assembly 248. The drive shaft 254 also advances the knife 255a and the actuation sled 266. The motor(s) 152a-d are activated at a setpoint speed, which may be received from the storage device 203 or any other location. In embodiments, the drive shaft 254 may be designed to only close closes the anvil assembly 246 and the cartridge assembly 248 and then advance the knife 255a and the actuation sled 266 after the anvil assembly 246 is closed. In further embodiments, another drive shaft may be used to advance the knife 255a and/or the actuation sled 266, either alone or in sequence. The present disclosure for stopping the drive shaft(s) may be applied to any drive shaft used in a stapling instrument.

During the firing process, the IDU controller 41d continuously monitors multiple parameters, such as motor position, which may be position of the motors 152a-d expressed as an angle θ, motor current draw, motor torque, which may be expressed as t. At step 306, the IDU controller 41d compares the measured motor position to a first position threshold, i.e., the first point 330, which may be stored in the storage device 203, locally, or in any other suitable manner. The first position threshold may be specific to one type of loading units 240 and may correspond to a motor position at which the drive shaft 254 is at a midpoint of the firing sequence. The first position threshold may also depend on the articulation of the end effector 244 as this bends the drive shaft 254 resulting in an offset of the actuation distances for staple ejection and end stop due to lengthening of the distance being traveled by the drive shaft 254 through the bend. The threshold value may be loaded from the storage device 203, 303, 403.

If the motor position is not past, i.e., less than, the first position threshold, then the motor(s) 152a-d continue to operate at the setpoint velocity to advance the drive shaft 254 at step 304. If the motor position is past, i.e., larger, than the first position threshold, then at step 308, the IDU controller 41d compares the measured motor position to a second position threshold, which may also be stored in the storage device 203, locally, or in any other suitable manner. The second position threshold may be also specific to one type of loading units 240 and may correspond to a motor position at which the drive shaft 254 is close to the end of the firing sequence, e.g., before the fourth point 334.

If the motor position is not past, i.e., less than, the second position threshold, then at step 310 the IDU controller 41d compares the measured motor torque to the maximum torque threshold. If the measured torque is less than the maximum torque, then the motor(s) 152a-d continue to operate at the setpoint velocity to advance the drive shaft 254 at step 304, and the method repeats as described above. However, if the measured torque is above the maximum torque threshold, then at step 312 the IDU controller 41d calculates a set stop position (i.e., fourth point 334) based on the current motor position and an offset value, which may be loaded from the storage device 303. In particular, the IDU controller 41d adds the offset value to the current motor position. The IDU controller 41d stores the current motor position which corresponds to the point in time at which the measured torque exceeded the maximum torque threshold. The IDU controller 41d then adds the offset value to the current motor position to determine the fourth point 334 at which to stop the firing process. The offset value may be stored in the storage device 303, locally, or in any other suitable manner.

At step 313, the IDU controller 41d sets a new maximum torque threshold as the current motor torque. Step 313 in combination with step 310 determine when the motor torque has reached a peak. After calculating and updating the stop position and the maximum torque threshold, the motor(s) 152a-d continue to operate at the setpoint velocity to advance the drive shaft 254 at step 304, and the method repeats as described above.

Upon reaching step 308 again, the IDU controller 41d compares the measured motor position to the second position threshold. If the motor position is past, i.e., larger than, the second position threshold, then at step 314 the IDU controller 41d compares the measured motor position to the stop position as calculated at step 312. If the motor position is not past, i.e., less than, the calculated stop position, then the motor(s) 152a-d continue to operate at the setpoint velocity to advance the drive shaft 254 at step 304, and the method repeats as described above. If the motor position is past, i.e., larger than, the calculated stop position, at step 316 the motor(s) 152a-d stop advancing the drive shaft 254. Upon reaching the stop position, the IDU controller 41d may output an indication, e.g., a prompt on the GUI, that the stapling process is complete. The IDU controller 41d may also automatically retract the drive shaft 254 to unclamp and open the end effector 244.

Figure 10:
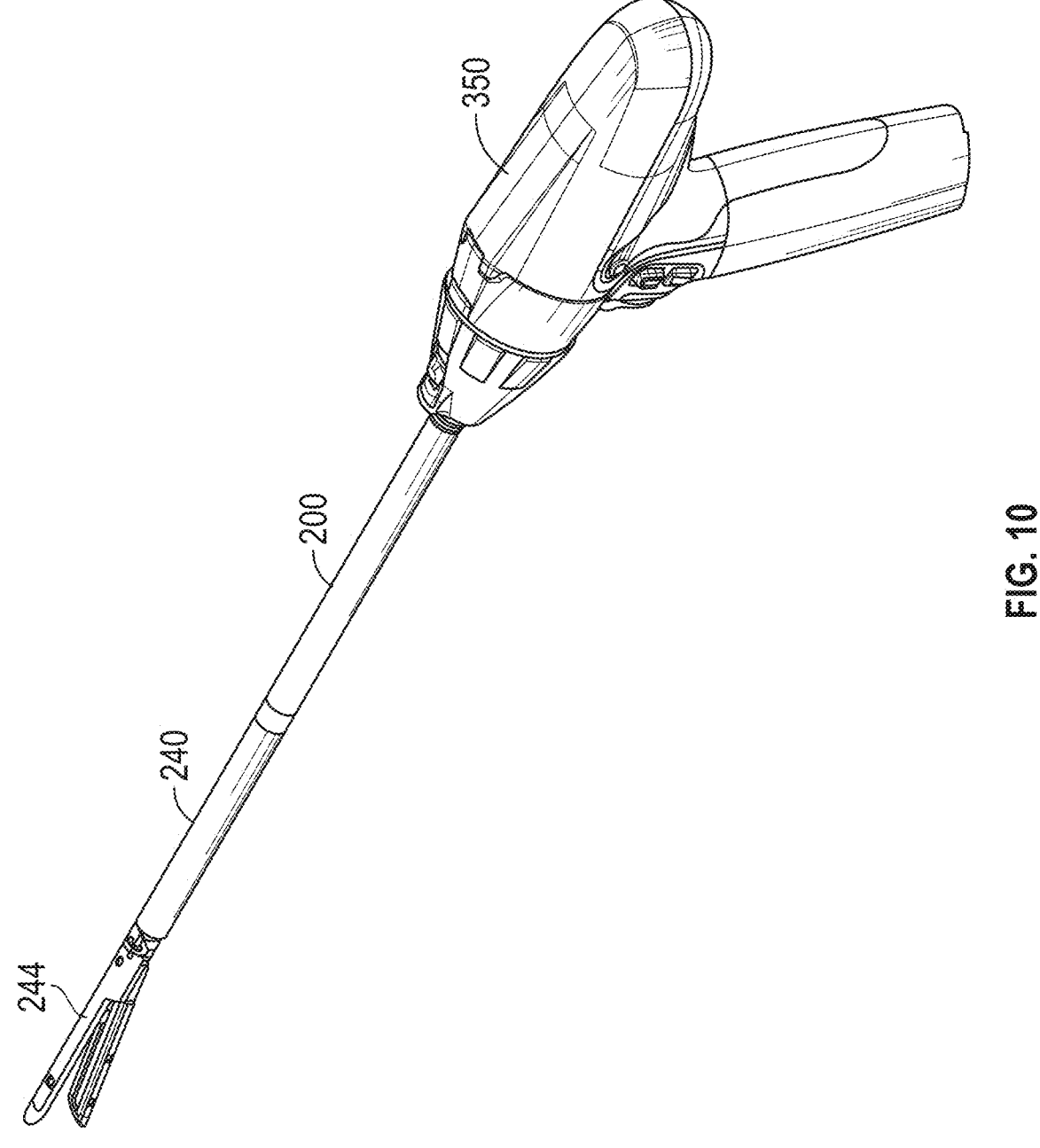
FIG. 10 is a perspective view of a powered handheld surgical device including the surgical instrument of FIG. 5 according to an embodiment of the present disclosure.

With reference to FIG. 10, the loading unit 240 may be used with a powered surgical handle 350, having similar components as the IDU 52, e.g., one or more motors, controllers, memory storing instructions, etc. The loading unit 240 is coupled via the adapter 200 to the handle 350, which controls the stapling process in the same manner described above.

Figure 11:
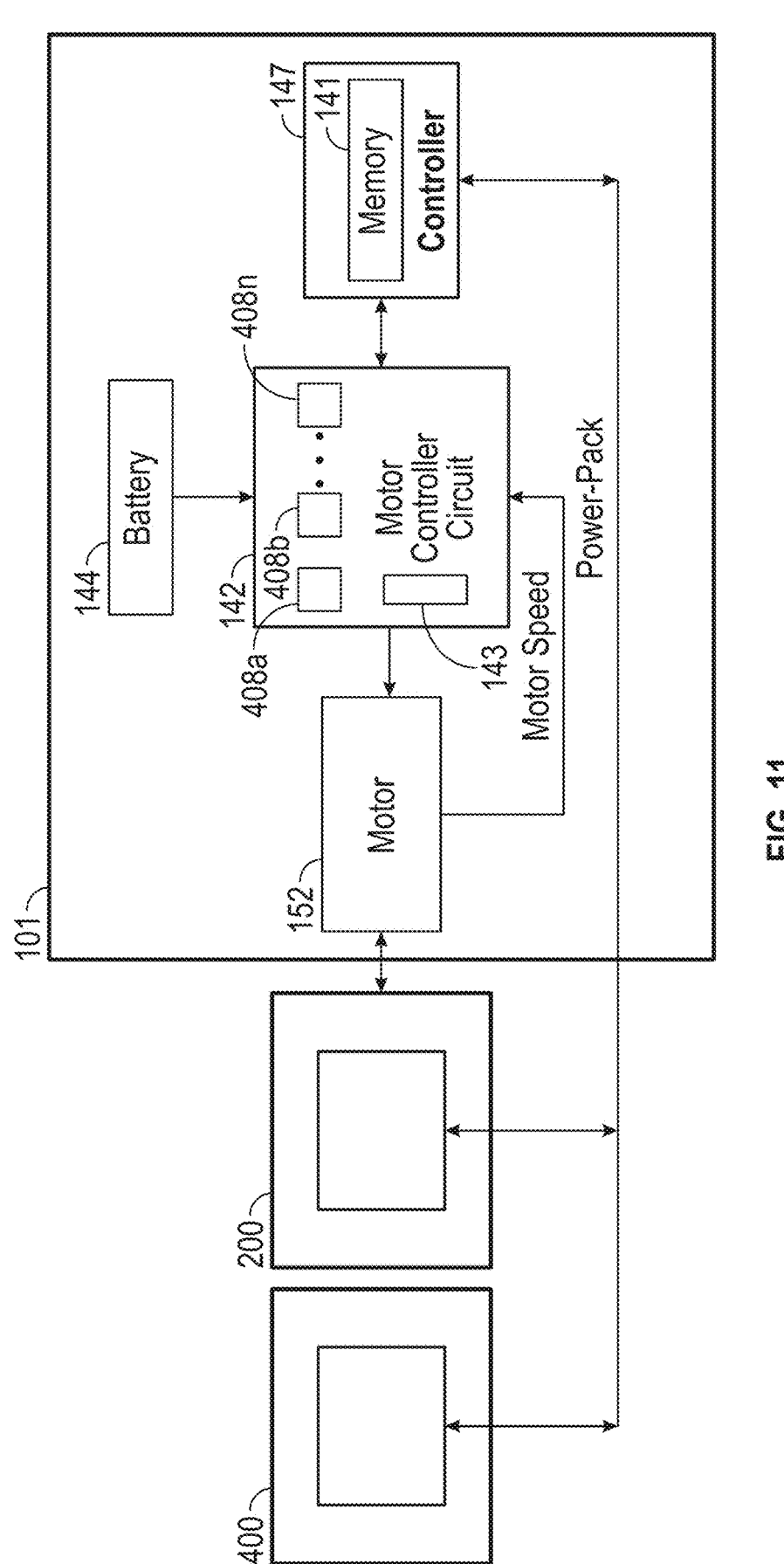
FIG. 11 is a schematic diagram of the powered handheld surgical device of FIG. 10.

FIG. 11 shows components to the handle 350 includes a main controller circuit board 142, a rechargeable battery 144 configured to supply power to any of the electrical components of handle 350, and a plurality of motors 152a-d coupled to the battery 144.

Each of the motors 152a-d includes a respective motor shaft (not explicitly shown) extending therefrom and configured to drive a respective transmission assembly disposed inside the adapter 200. Rotation of the motor shafts (by the respective motors) functions to actuate cables, drive shafts, gears, and other mechanical drive components of adapter 200 in order to perform the various operations of handle 350 to actuate the end effector 244.

The motors 152a-d may be coupled to any suitable power source configured to provide electrical energy to the motors 152a-d, such as an AC/DC transformer. Each of the motors 152a-d is coupled a motor controller 143 which controls the operation of the corresponding motors 152a-d including the flow of electrical energy from the battery 144 to the motors 152a-d. A main controller 147 is provided that controls the handle 350. The main controller 147 is configured to execute software instructions embodying algorithms, such as clamping, stapling, and cutting algorithms which control operation of the handle 350. The handle 350 may also include a display.

The motor controller 143 includes a plurality of sensors 160a . . . 160n configured to measure operational states of the motors 152a-d and the battery 144. The sensors 160a-n include a strain gauge 160b and may also include voltage sensors, current sensors, temperature sensors, telemetry sensors, optical sensors, torque sensors, and combinations thereof. The strain gauge 160b may be disposed within the adapter 200. The sensors 160a-160n may measure voltage, current, and other electrical properties of the electrical energy supplied by the battery 144. The sensors 160a-160n may also measure angular velocity (e.g., rotational speed) as revolutions per minute (RPM), torque, temperature, current draw, and other operational properties of the motors 152a-d. The sensor 160a also includes an encoder configured to count revolutions or other indicators of the motors 152a-d, which is then used by the main controller 147 to calculate linear movement of components movable by the motors 152a-d. Angular velocity may be determined by measuring the rotation of the motors 152a-d or a drive shaft (not shown) coupled thereto and rotatable by the motors 152a-d. The position of various axially movable drive shafts may also be determined by using various linear sensors disposed in or in proximity to the shafts or extrapolated from the RPM or position measurements. In embodiments, torque may be calculated based on the regulated current draw of the motors 152a-d at a constant RPM. In further embodiments, the motor controller 143 and/or the main controller 147 may measure time and process the above-described values as a function of time, including integration and/or differentiation, e.g., to determine the rate of change in the measured values. The main controller 147 is also configured to determine distance traveled of various components of the adapter 200 and/or the end effector 244 by counting revolutions of the motors 152a-d.

The motor controller 143 is coupled to the main controller 147, which includes a plurality of inputs and outputs for interfacing with the motor controller 143. In particular, the main controller 147 receives measured sensor signals from the motor controller 143 regarding operational status of the motors 152a-d and the battery 144 and, in turn, outputs control signals to the motor controller 143 to control the operation of the motors 152a-d based on the sensor readings and specific algorithm instructions. The main controller 147 is also configured to accept a plurality of user inputs from a user interface (e.g., switches, buttons, touch screen, etc.) coupled to the main controller 147.

The main controller 147 is also coupled to a memory 141. The memory 141 may include volatile (e.g., RAM) and non-volatile storage configured to store data, including software instructions for operating the handle 350. The main controller 147 is also coupled to the strain gauge 160b using a wired or a wireless connection and is configured to receive strain measurements from the strain gauge 160b which are used during operation of the handle 350. The disclosed algorithm may be applied to any articulatable powered or robotic end effectors, such as vessel sealers having a knife movable through a pair of opposing jaw members.

With reference to FIG. 12, another algorithm according to the present disclosure for controlling operation of a robotic or powered stapler is disclosed. The algorithm may be embodied as software instructions stored in a non-transitory computer readable medium and executable by a processor, e.g., controller 21a, IDU controller 41d, etc.

During the stapling process, motor parameter (e.g., current, torque, etc.) peaks are generated as the drive shaft 254 advances the actuation sled 266 through the staple cartridge 258. As the sled 266 moves forward, its cam wedges engage the staple pushers 264, driving the staples 262 upward and forming them against the anvil plate 246a of the anvil assembly 246. The resistance encountered as the staples 262 are ejected into tissue and formed against the anvil results in an increase in the force required to move the drive shaft 254. This increased force causes a corresponding spike in the motor parameters, which is measured by the torque sensor 155 or any other motor sensor. Each staple ejection produces a similar peak, creating a repetitive pattern as the actuation sled 266 advances through the staple cartridge 258. This process can also be applied to incorporate valleys in the plot, or other signal landmarks.

According to another embodiment of the present disclosure, one or more fiducials 259 may be tracked during stapling operation to determine an end stop. The fiducial 259 may be a physical marker, which can cause a detectable increase in force measured by any of the sensors disclosed herein, such as a motor current sensor, torque sensor, strain gauge, load cell, etc. The fiducial 259 may be a structure that interferes with the movement of the drive shaft 254 or the knife 255a, resulting in deformation and a corresponding force spike. Thus, the fiducial 259 is a feature at a fixed distance within the staple cartridge 258, allowing for the establishment of an offset relative to the end of the staple cartridge 258. Examples of fiducials 259 may include an indentation in the anvil that the drive shaft 254 traverses, or a narrowing in the longitudinal slot 258a of the staple cartridge 258. The first position may correspond to a staple formation, which occurs at fixed intervals. This position can be continuously updated by detecting the next peak in force and adjusting the predicted end stop accordingly. Additionally, multiple fiducials may be embedded within the staple cartridge 258 to further refine positional accuracy.

The process may use a linear quadratic estimation algorithm, such as Kalman filtering to determine the end stop. Initially, an estimated end stop position (X) and the corresponding error (E) are calculated based on the staple cartridge 258 configuration and articulation state. Additionally, a range is defined for the location of the first expected staple peak (P). Once the first staple peak is identified, the system updates the predicted end stop position ($\dot{X}$) based on this measurement and estimates the position of the next staple peak. This updated prediction is compared to the previous end stop estimate. The gain (G) is calculated based on the difference between the new and previous estimates, using the known empirical errors in the peak measurement (R) and the end stop calculation (Q). The gain is then applied to the difference between the new and old estimates, resulting in an updated end stop prediction. The error is also updated using the new measurements. This method ensures that each new measurement increases the accuracy of the end stop prediction. Furthermore, the error in the measurement may be used to establish a potential cardinal zone or trigger adjustments if the error exceeds a predefined threshold.

At step 400, input parameters, such as staple cartridge 258 length, staple size, number of staples, and articulation state are loaded from the storage device 303, 403, or any other storage device. The parameters are used for determining the initial estimated end stop position ($X_0$) and the corresponding error ($E_0$).

At step 402, the processor calculates an initial estimate of the end stop position ($X_0$) and its error ($E_0$) based on the received input parameters from step 400. This provides the starting point for predicting the end stop during the stapling process.

At step 404, the processor sets a counter (k) is initialized to 1 to keep track of peaks, valleys, valleys, or other signal landmarks. This step marks the start of the iterative process for detecting and processing staple peaks during the stapling cycle. The step includes monitoring a motor or mechanical parameter that is affected by staple ejection, e.g., torque, current draw, force, etc. and tracking the parameter overtime to detect the signal landmarks, e.g., peaks. The counter (k) may be initialized to 1 prior to detecting the first peak.

At step 406, the processor establishes, i.e., sets, a position range (e.g., length of travel through the staple cartridge 258) during which the peak is expected to be detected. The position range may be expressed as a starting and an ending distance values ($P_{kL}$, $P_{kH}$) for a particular staple peak (k). This range is based on the position of the previous staple peak ($L_{k-1}$), if known (i.e., second or later peak), or the initial estimate of the end stop ($X_o$) if no prior peak data is available (i.e., first peak).

At step 408, the processor detects staple peak Location ($L_k$) within the position range ($P_{kL}$, $P_{kH}$). The processor searches for and detects the location of the $k^{th}$ staple peak ($L_k$) within the specified position range ($P_{kL}$, $P_{kH}$). This is accomplished using real-time sensor data, such as motor torque, current draw, force measurements, etc. to identify the peak corresponding to the staple formation.

At step 410, the processor calculates a new measurement of the end stop ($\dot{X}_k$) from the detected peak $L_k$. Once the $k^{th}$ staple peak ($L_k$) is detected, the processor updates the end stop position prediction to $\dot{X}_k$, incorporating the new distance measurement from the detected staple peak.

At step 412, the processor determines a gain value (G) from previous error ($E_{k-1}$) and estimates an optimized measurement error. The gain (G) is computed based on the previous error ($E_{k-1}$), if any, and the empirical errors in the peak measurement and end stop calculation. The gain (G) of the difference between then new estimate and the old estimate is determined based on the previous error combined with the error in the peak measurement and the error in the calculation of the end stop. The gain acts as a weighing factor assigned to the new distance measurement of the peak to refine the end stop estimate.

During steps 414 and 416, the gain (G) is used to adjust the end stop ($X_k$) and the error value ($E_k$). The gain is applied to the difference between the old estimate and new estimate and added to the old estimate to determine an updated estimate. At step 414 an updated estimate of the end stop ($X_k$) is calculated from the previous and newly acquired estimates. The end stop estimate ($X_k$) is updated by applying the gain (G) to the difference between the new measurement ($\dot{X}_k$) and the previous estimate ($X_{k-1}$), which may be expressed as:

$$X_k = X_{k-1} + G(\dot{X} - X_{k-1})$$

At step 416, an updated new estimate of error ($E_k$) is calculated from the previous and newly acquired error. The new error estimate ($E_k$) is updated based on the gain (G) and the previous error ($E_{k-1}$). This reflects the reduction in uncertainty after incorporating the new measurement, which may be expressed by:

$$E_k = E_{k-1} + G(E_{k-1})$$

At step 418, the counter (k) is incremented, e.g., k=k+1. At step 420, the IDU controller 41d compares the measured motor position to the updated estimate of the end stop as calculated at step 414. If the motor position is not past, i.e., less than, the calculated stop position, then the motor(s) 152a-d continue to operate at the setpoint velocity to advance the drive shaft 254, and the method repeats from step 406 to continue refining the end stop prediction for the next detected staple peak until the end of the stapling cycle is reached.

If the motor position is past, i.e., larger than, the updated estimate of the end stop, at step 422 the motor(s) 152a-d stop advancing the drive shaft 254. Upon reaching the stop position, the IDU controller 41d may output an indication, e.g., a prompt on the GUI, that the stapling process is complete. The IDU controller 41d may also automatically retract the drive shaft 254 to unclamp and open the end effector 244.

This iterative process allows for progressively more accurate estimations of the end stop with each staple peak detected. Furthermore, the error in the measurement can be used to define a potential cardinal zone, should the error exceed a certain threshold. This method ensures greater precision in the location of the end stop. In addition, the method of FIG. 12 may also be used to track number of staple ejections to confirm that each row of the staples was ejected. Furthermore, where a buttress (not shown) is secure to the staple cartridge 258 using one or more sutures, as the knife is advanced, the suture cutting events may also be monitored using this method.

It will be understood that various modifications may be made to the embodiments disclosed herein. In embodiments, the sensors may be disposed on any suitable portion of the robotic arm or stapling adapter. Therefore, the above description should not be construed as limiting, but merely as exemplifications of various embodiments. Those skilled in the art will envision other modifications within the scope and spirit of the claims appended thereto.

What is claimed is:

1. A surgical robotic system comprising:
   a robotic arm including an instrument drive unit having a motor;
   a loading unit coupled to the motor, the loading unit including:
   an end effector having a first jaw and a second jaw; and
   a drive shaft movable through the end effector approximating at least one of the first jaw or the second jaw relative to each other;
   a sensor for measuring an actuation parameter; and
   a controller for:
   receiving the actuation parameter and determining a first position of the drive shaft based on the actuation parameter;
   calculating a stop position for the drive shaft that occurs prior to reaching a mechanical limit of the drive shaft, wherein the controller calculates the stop position by adding an offset value to the first position; and
   stopping the motor such that the drive shaft stops at the stop position.

2. The surgical robotic system according to claim 1, wherein the sensor is at least one of a motor torque sensor, a motor current sensor, or a strain sensor.

3. The surgical robotic system according to claim 1, wherein the actuation parameter is at least one of motor torque, current draw, or strain.

4. The surgical robotic system according to claim 1, wherein the instrument drive unit further includes a position sensor for measuring a position of the motor.

5. The surgical robotic system according to claim 4, further comprising a storage device storing a maximum threshold value and the offset value, wherein the storage device is accessible by the controller.

6. The surgical robotic system according to claim 5, wherein the controller determines the first position based on the position of the motor at a point in time when the actuation parameter exceeds the maximum threshold value.

7. A powered surgical stapler comprising:

a motor and a sensor for measuring an actuation parameter;

a loading unit coupled to the motor, the loading unit including:

an end effector having a first jaw and a second jaw; and a drive shaft movable through the end effector for approximating at least one of the first jaw or the second jaw relative to each other; and a controller for:

receiving the actuation parameter and determining a first position of the drive shaft based on the actuation parameter;

calculating a stop position for the drive shaft that occurs prior to reaching a mechanical limit of the drive shaft, wherein the controller calculates the stop position by adding an offset value to the first position; and stopping the motor such that the drive shaft stops at the stop position.

8. The powered surgical stapler according to claim 7, wherein the sensor is at least one of a motor torque sensor, a motor current sensor, or a strain sensor.

9. The powered surgical stapler according to claim 7, wherein the actuation parameter is at least one of motor torque, current draw, or strain.

10. The powered surgical stapler according to claim 7, further comprising a position sensor for measuring a position of the motor.

11. The powered surgical stapler according to claim 10, further comprising a storage device storing a maximum threshold value and the offset value, wherein the storage device is accessible by the controller.

12. The powered surgical stapler according to claim 11, wherein the controller determines the first position based on the position of the motor at a point in time when the actuation parameter exceeds the maximum threshold value.

13. A system for controlling an end effector of a surgical stapling instrument, comprising:

a stapling instrument including an end effector having an anvil and a staple cartridge with a plurality of staples, wherein at least one of the anvil or the staple cartridge are movable relative to each other;

a drive shaft movable through the end effector to eject the plurality of staples;

a motor for actuating the drive shaft;

a sensor configured to measure an actuation parameter associated with at least one of the drive shaft or the motor during ejection of the plurality of staples; and a controller configured to:

receive the actuation parameter from the sensor;

detect multiple signal events corresponding to at least one of a peak or a valley in the actuation parameter, wherein the signal events are caused by staple ejections;

estimate an end stop position for the drive shaft that occurs prior to reaching a mechanical limit of the drive shaft based on at least one of the signal events;

continuously update the estimated end stop position based on at least another one of the signal events;

determine a final end stop position based the estimated end stop position before the drive shaft reaches a mechanical limit; and generate a stop command to stop the motor when the final end stop position is reached.

14. The system according to claim 13, wherein the drive shaft is further configured to approximate at least one of the anvil or the staple cartridge relative to each other.

15. The system according to claim 13, wherein the controller is further configured to use a sequential Kalman filtering process.

16. The system according to claim 13, wherein the controller is further configured to calculate an error between a prior estimated end stop position and a current estimated end stop position.

17. The system according to claim 16, wherein the controller is further configured to calculate a gain value and update the estimated end stop position by adding a gain-multiplied difference between the prior estimated end stop position and the current estimated end stop position to the current estimated end stop position.

* * * * *